United States Patent [19]

Ermann et al.

[11] Patent Number: 5,318,963
[45] Date of Patent: Jun. 7, 1994

[54] HETEROCYCLIC HYDRAZIDE DERIVATIVES OF MONOCYCLIC β-LACTAM ANTIBIOTICS

[75] Inventors: Peter H. Ermann, Donaustauf; Henner Straub, Regensburg, both of Fed. Rep. of Germany

[73] Assignee: E. R. Squibb & Sons, Inc., Princeton, N.J.

[21] Appl. No.: 620,170

[22] Filed: Nov. 30, 1990

Related U.S. Application Data

[63] Continuation-in-part of Ser. No. 410,217, Sep. 21, 1989, abandoned.

[51] Int. Cl.$^5$ ............... C07D 205/085; C07D 417/14; A61K 31/47; A61K 31/425
[52] U.S. Cl. .................................... 514/210; 540/355
[58] Field of Search ........................ 514/210; 540/355

[56] References Cited

U.S. PATENT DOCUMENTS

| | | | |
|---|---|---|---|
| 4,217,453 | 8/1980 | Christensen et al. | 544/373 |
| 4,224,336 | 9/1980 | Christensen et al. | 424/274 |
| 4,587,047 | 5/1986 | Breuer et al. | 260/239 A |
| 4,610,824 | 9/1986 | Truner | 540/355 |
| 4,670,553 | 6/1987 | Breuer et al. | 540/363 |
| 4,743,685 | 5/1988 | Breuer et al. | 540/363 |
| 4,772,693 | 9/1988 | Breuer | 540/363 |
| 4,775,670 | 10/1988 | Sykes et al. | 514/210 |
| 4,904,775 | 2/1990 | Sundeen | 540/363 |
| 4,959,470 | 9/1990 | Treuner | 540/363 |
| 5,030,724 | 7/1991 | Sundeen | 540/355 |
| 5,037,983 | 8/1991 | Sundeen | 540/355 |

FOREIGN PATENT DOCUMENTS

| | | |
|---|---|---|
| 0254495 | 1/1988 | European Pat. Off. |
| 0010426 | 4/1988 | European Pat. Off. |
| 0304158 | 7/1988 | European Pat. Off. |
| 342423 | 11/1989 | European Pat. Off. |

OTHER PUBLICATIONS

Mochida, et al.; Journal of Antibiotics, Feb. 1987, pp. 182-189.

Mochida, et al.; Journal of Antibiotics, Jan. 1987, pp. 14-21.

Primary Examiner—Mark L. Berch
Attorney, Agent, or Firm—Timothy J. Gaul

[57] ABSTRACT

Antibacterial activity has been found in compounds of the formula.

Compounds having the formula

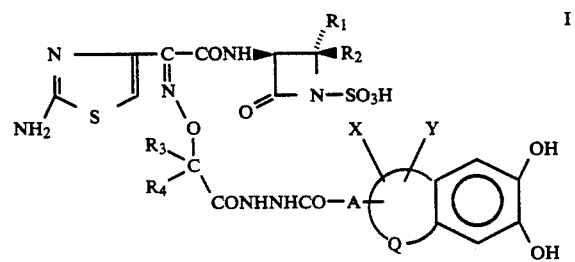

and pharmaceutically acceptable salts thereof, wherein:
A is a bond or alkylene;
Q completes a 5- or 6-membered saturated or unsaturated (including aromatic) heterocyclic ring having one or two, heteroatoms in the ring selected from nitrogen,

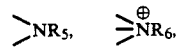

sulfur or oxygen;
X is attached to an available carbon atom in the heterocyclic ring and is hydrogen or oxo;
Y is attached to an available carbon atom in the heterocyclic ring and is hydrogen, amino, hydroxyl, halogen, carboxamide, nitrile, or carboxyl, except that Y is not carboxyl when the bicyclic ring completed by Q is 2-quinolyl, 3-quinolyl, or quinoxalyl;
and the remaining symbols are as defined in the specification.

13 Claims, No Drawings

HETEROCYCLIC HYDRAZIDE DERIVATIVES OF MONOCYCLIC β-LACTAM ANTIBIOTICS

This application is a continuation-in-part of U.S. Ser. No. 410,217, filed Sep. 21, 1989, abandoned.

FIELD OF THE INVENTION

This invention relates to antibacterial agents and, in particular, to β-lactams.

BRIEF DESCRIPTION OF THE INVENTION

Compounds having the formula

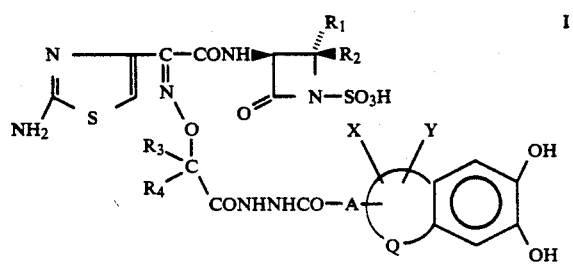

and pharmaceutically acceptable salts thereof exhibit antibacterial activity. In formula I, and throughout the specification, the symbols are as defined below:

A is a bond or alkylene;

Q completes a 5- or 6-membered saturated or unsaturated (including aromatic) heterocyclic ring having one or two heteroatoms in the ring selected from nitrogen,

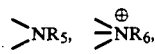

sulfur, or oxygen;

X is attached to an available carbon atom in the heterocyclic ring and is hydrogen or oxo;

Y is attached to an available carbon atom in the heterocyclic ring and is hydrogen, amino, hydroxyl, halogen, carboxamide, nitrile, or carboxyl, provided that Y is not carboxyl when

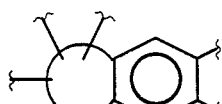

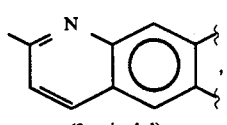
(2-quinolyl) or quinoxalyl;

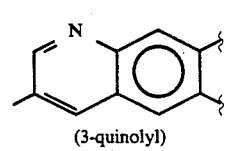
(3-quinolyl)

$R_1$ and $R_2$ are the same or different and each is independently hydrogen, alkyl, alkenyl, alkynyl, cycloalkyl, phenyl, substituted phenyl, or $R_7$; or one of $R_1$ and $R_2$ is hydrogen and the other is azido, halomethyl, dihalomethyl, trihalomethyl, alkoxycarbonyl, 2-phenylethenyl, 2-phenylethynyl, carboxyl, —CH$_2$X$_1$, —S—X$_2$, O—X$_2$,

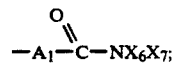

$R_3$ and $R_4$ are the same or different and each is hydrogen or alkyl; or $R_3$ and $R_4$, together with the carbon atom to which they are attached, are cycloalkyl;

$R_5$ is hydrogen, lower alkyl, cycloalkyl, hydroxyl, amino, or carboxyalkyl;

$R_6$ is hydrogen, lower alkyl, cycloalkyl, carboxyalkyl, or oxide;

$R_7$ is a 4, 5, 6 or 7-membered heterocycle;

$X_1$ is azido, amino, hydroxyl,

alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

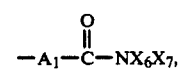

—S—X$_2$, or —O—X$_2$;

$X_2$ is alkyl, substituted alkyl, phenyl, substituted phenyl, phenylalkyl, (substituted phenyl)alkyl, alkanoyl, substituted alkanoyl, phenylalkanoyl, (substituted phenyl)alkanoyl, phenylcarbonyl, (substituted phenyl)carbonyl, or heteroarylcarbonyl; and when $X_1$ is O—X$_2$, then $X_2$ can also be alkylideneamino, alkanoylamino, carboxyalkylideneamino, alkylsulfonylamino, alkoxycarbonyl-alkylsulfonylamino or N,N-cyclodialkanoylamino),

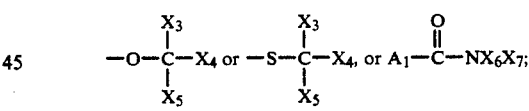

one of $X_3$ and $X_4$ is hydrogen and the other is hydrogen or alkyl; or $X_3$ and $X_4$, taken together with the carbon atom to which they are attached, form a cycloalkyl group;

$X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano;

$X_6$ and $X_7$ are the same or different and each is hydrogen, alkyl, phenyl or substituted phenyl; or $X_6$ is hydrogen and $X_7$ is amino, substituted amino, alkanoylamino or alkoxy; or $X_6$ and $X_7$, taken together with the nitrogen atom to which they are attached, form a 4, 5, 6 or 7-membered heterocycle;

$A_1$ is —CH=CH—, —(CH$_2$)$_m$—, —(CH$_2$)$_m$—O—, —(CH$_2$)$_m$—NH—, or —CH$_2$—S—CH$_2$—; and m is 0, 1 or 2.

Preferred compounds are those in which:

$R_1$ is hydrogen or alkyl;

$R_2$ is hydrogen or alkyl;
one of $R_1$ and $R_2$ is hydrogen and the other is alkyl;
$R_3$ is hydrogen or alkyl;
$R_4$ is hydrogen or alkyl;
$R_3$ and $R_4$ are both hydrogen or both alkyl;
Y is hydrogen, hydroxyl, or carboxyl;
A is a bond or methylene; and
the heterocyclic ring defined by Q comprises

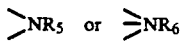

wherein in $R_5$ is hydrogen, carboxyalkyl, or hydroxyl, and $R_6$ is methyl, carboxyalkyl, or oxide.

Also preferred are compounds in which the heterocyclic ring has one or two nitrogen atoms or one oxygen atom or one sulfur atom in the ring.

Most preferred are compounds in which:

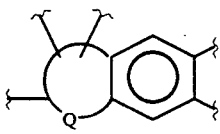

is saturated or unsaturated quinolyl, isoquinolyl, quinoxalyl, cinnolyl, benzofuranyl, isoindolyl, or isoindolinium;
$R_1$ is hydrogen or methyl;
$R_2$ is hydrogen or methyl;
one of $R_1$ and $R_2$ is hydrogen and the other is methyl;
$R_3$ is hydrogen or methyl;
$R_4$ is hydrogen or methyl; and
the heterocyclic ring defined by Q comprises $NR_5$ and $R_5$ is carboxymethyl.

DETAILED DESCRIPTION OF THE INVENTION DEFINITION OF TERMS

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy", individually or as part of a larger group, refer to both straight and branched chain groups. Those groups having 1 to 10 carbon atoms are preferred. Exemplary alkyl groups are methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodedcyl, the various branched chain isomers thereof, and the like.

The term "aryl" refers to phenyl and substituted phenyl (see definition below).

The term "cycloalkyl", individually or as part of a larger group, refers to saturated cyclic hydrocarbon groups having 3, 4, 5, 6 or 7 carbon atoms. Exemplary cycloalkyl groups are cyclopropyl, cyclobutyl, cyclopentyl, cyclohexyl, cycloheptyl, cyclooctyl, cyclodecyl and cyclododecyl.

The term "substituted alkyl" refers to alkyl groups substituted with one or more (preferably 1, 2, or 3) azido, amino, halogen, hydroxyl, carboxyl, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups.

The terms "alkanoyl", "alkenyl", and "alkynyl" individually or as part of a larger group refer to both straight and branched chain groups. Those groups having 2 to 10 carbon atoms are preferred.

The term "substituted alkanoyl" refers to alkanoyl groups substituted with one or more (preferably 1, 2 or 3) azido, amino, halogen, hydroxyl, carboxyl, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl or alkylsulfonyl groups.

The term "substituted phenyl" refers to a is phenyl group substituted with 1, 2 or 3 amino, halogen, hydroxyl, trifluoromethyl, alkyl (of 1 to 4 carbon atoms), alkoxy (of 1 to 4 carbon atoms), alkanoyloxy, aminocarbonyl, or carboxyl groups.

The expression "a 5- or 6-membered saturated or aromatic heterocyclic ring" refers to substituted and unsubstituted, aromatic and non-aromatic cyclic groups. One type of such a heterocyclic ring is a "heteroaryl" group (see definition below).

The expression "a 4, 5, 6 or 7-membered heterocycle" refers to substituted and unsubstituted, monocyclic and bicyclic, aromatic and non-aromatic groups containing one to four nitrogen atoms and/or one or two oxygen or sulfur atoms. Exemplary substituents are oxo (═O), halogen, hydroxyl, nitro, amino, cyano, trifluoromethyl, alkyl of 1 to 4 carbons, alkoxy of 1 to 4 carbons, alkylsulfonyl, phenyl, substituted phenyl, 2-furfurylideneamino

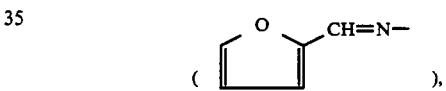

benzylideneamino and substituted alkyl groups (wherein the alkyl group has 1 to 4 carbons). One type of "4, 5, 6 or 7-membered heterocycle" is the "heteroaryl" group (see definition below).

The term "heteroaryl" refers to those 4, 5, 6 or 7-membered heterocycles that are aromatic. Exemplary heteroaryl groups are substituted and unsubstituted pyridinyl, furanyl, pyrrolyl, thienyl, 1, 2, 3-triazolyl, 1, 2, 4-triazolyl, imidazolyl, thiazolyl, thiadiazolyl, pyrimidinyl, oxazolyl, triazinyl, and tetrazolyl.

Exemplary non-aromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4, 5, 6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)aminol-2-oxo-1-imidazolidinyl, 3-[2-[(alkoxycarbonyl)amino]ethyl]-2-oxo-1-imidazolidinyl], 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl- 2,3-dioxo-1-piperazinyl, and 4-phenyl-2,3-dioxo-1-piperazinyl.

The terms "halogen" or "halo" refer to fluorine, chlorine, bromine and iodine.

The term "substituted amino" refers to a group having the formula —NX$_8$X$_9$ wherein X$_8$ is hydrogen, alkyl, phenyl, substituted phenyl, phenylalkyl or (substituted phenyl)alkyl, and X$_9$ is alkyl, phenyl, substituted phenyl, phenylalkyl, (substituted phenyl)alkyl, hydroxy, cyano, alkoxy, phenylalkoxy, or amino.

The compounds of this invention form basic salts with inorganic and organic bases. These salts are included within the language "pharmaceutically acceptable salts" and are within the scope of this invention. Such salts include ammonium salts, alkali metal salts, alkaline earth metal salts, and salts with organic bases such as is dicyclohexylamine, benzathine, N-methyl-D-gluccamine, hydroxyamine and the like.

The compounds of this invention are pictured as acids. They can also exist, however, as zwitterions (internal or inner salts), and these are also included within the language "pharmaceutically acceptable salts" and the scope of this invention.

USE AND UTILITY

The β-lactams of formula I, and pharmaceutically acceptable salts thereof, have activity against gram-positive and gram-negative organisms. Of particular interest is the good activity against gram-negative organisms in vitro and in vivo exhibited by the compounds of this invention. The compounds of this invention can be used as agents to combat bacterial infections (including urinary tract infections and respiratory infections) in mammalian species, such as domesticated animals (e.g., dogs, cats, cows, horses, and the like) and humans.

For combatting bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the β-lactams of this invention. Such methods of administration include oral, intravenous, and intramuscular, and as a suppository.

PROCESS OF PREPARATION

Formula I compounds may be prepared by coupling a novel hydrazide compound of the formula

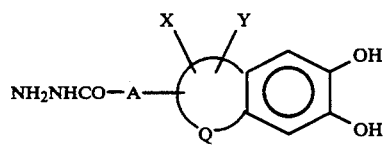

II with a β-lactam having a sulfonic acid salt substituent (SO$_3$⊕M⊖ wherein M⊕ is hydrogen or a pharmaceutically acceptable cation) in the 1-position and an amino substituent in the 3-position (see U.S. Pat. No. 4,775,670). This process is further described in Methods A and B hereafter. Alternatively, a formula I compound may be formed by coupling a novel quinolone-dicarboxylic acid of the formula

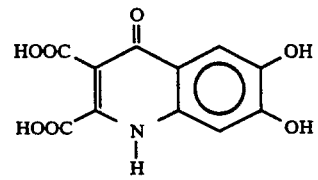

IIIa with a β-lactam hydrazide of the formula

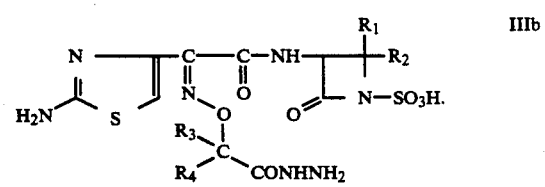

IIIb

The latter process is further described in Method C hereafter. Preparation of compound IIIb is described in U.S. Pat. No. 4,610,824 and in Examples 8a and 8b hereafter. Compounds II and IIIa are novel and form an integral part of this invention.

METHOD A

A formula I compound may be prepared from compound II as follows. Compound II may be treated with a persilylating agent (e.g., N-methyl-N-trimethylsilyl-trifluoroacetamide) in an organic solvent (e.g., acetonitrile, dimethylformamide, or dimethylsulfoxide). The above-described β-lactam may be treated with such reactants as tributylamine, hydroxybenzotriazole, dicyclohexylcarbodiimide, and dimethylaminopyridine in an organic solvent (e.g., dimethylformamide or dimethylsulfoxide). The so-treated β-lactam may then be treated with compound II in an organic solvent (e.g., dimethylformamide or dimethylsulfoxide) at about room temperature to yield a compound of formula I.

When A is a bond (e.g., Examples 1, 2, 3, 4, 5, 6, 7, 9, and 10 hereinafter), compound II may be derived from the protected dihydroxy heterocyclic carboxylic acid compound of the formula

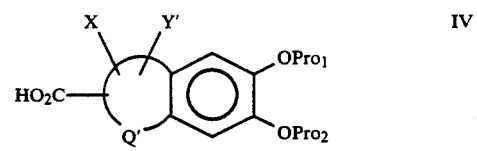

IV wherein Q' is Q or a combination of Q and a suitable protecting group and Y' is Y or a combination of Y and a suitable protecting group and Pro$_1$ and Pro$_2$ are suitable phenol protecting groups such as methyl or benzyl, or Pro$_1$ and Pro$_2$ together are a suitable catechol protecting group such as $$-CH_2-  \quad \text{or} \quad  \overset{|}{\underset{|}{C}}(CH_3)_2.$$

Compound II may be derived from compound IV by coupling compound IV with a protected hydrazide, followed by deprotection. Compound IV may be coupled with a protected hydrazide by treatment in an organic solvent (e.g., dimethylformamide) in two steps:

(a) first with such reactants as diphenylchlorophosphate, triethylamine, dicyclohexylcarbodiimide, dimethylaminopyridine, and hydroxybenzotriazole; and (b) followed by such reactants as t-butylcarbazate and benzylcarbazate. The protected compound IV may then be deprotected by catalytic hydrogenation or by treatment in an organic solvent (e.g., dimethylformamide, methylene chloride, and toluene) with such reactants as boron tribromide.

Compound IV may be prepared by a variety of methods. See, for example, the following references:

Riegel, B. et al., *J. Am. Chem. Soc.*, 68 (1946), 1264;
Ahmad, Y and Shamsi, S. A., *Bull. Chem. Soc. Jap.* 39 (1966), 195;
Schofield, K. and Simpson, J. C. E., *J. Chem. Soc.* 512 (1945);
Singh, G., Nair, G. V., and Aggarwal, K. P., *J. Sci. Ind. Research*, 15B (1956), 190; and
U.S. Pat. No. 4,777,252 (issued Oct. 11, 1988).

The literature does not disclose preparation of the novel compounds

[Structure IVa: quinoline N-oxide with HOOC, three OCH₃ groups]

and

[Structure IVb: HOOC-substituted quinolone with two OCH₂—C₆H₅ groups]

Preparation of these compounds is described in Examples 6 and 7 hereinafter. Compounds IVa and IVb are novel and form an integral part of this invention.

In the particular case where compound II follows the formula

[Structure IIa: NH₂NHCO-substituted quinoxaline diol]

compound II may be prepared as described in Example 4 hereinafter.

METHOD B

When A is —CH₂— (e.g., Examples 11 and 12 hereinafter), formula II compounds may be derived from compounds of the formula

[Structure V: $Pro_3$—NHNHCO—$CH_2$—$N^{\oplus}(R_6)$-benzyl with two OCH₃, Halo⊖]

wherein $Pro_3$ is a protecting group (e.g., benzyloxycarbonyl), and $R_6$ is hydrogen or alkyl. Compound V may be deprotected by treatment with, for example, boron tribromide in an organic solvent (e.g., methylene chloride) to yield compound II.

When $R_6$ is hydrogen, compound V may be derived from a compound of the formula

[Structure VIa: $Pro_4$—N-isoindoline with two OCH₃]

wherein $Pro_4$ is benzyl. To form compound V, compound VIa may be alkylated with a protected haloacetic acid hydrazide and then hydrogenated in an organic solvent (e.g., dimethylformamide) in the presence of a catalyst (e.g., palladium on charcoal).

When $R_6$ is alkyl, compound VI may be treated with a haloalkyl in an organic solvent (e.g., ether) to yield a salt of the formula

[Structure VIb: $Pro_4$—$N^{\oplus}(R_6)$-isoindoline with two OCH₃, Halo⊖]

Salt VIb, may undergo catalytic hydrogenation (e.g., with $H_2$ in the presence of palladium on charcoal), followed by neutralization (e.g., with aqueous sodium hydroxide) to yield

[Structure VIc: $R_6$—N-isoindoline with two OCH₃]

Compound VIc may be treated with Halo—CH₂—CO—NHNH—$Pro_3$ in an organic solvent (e.g., tetrahydrofuran:ether) to yield compound V. Compound II may be prepared from compound V as described above.

When $R_6$ is alkyl, compound II may also be prepared from the free base of compound V. The free base may be treated with a haloalkyl in an organic solvent (e.g., ether) followed by deprotection as described above (e.g., with boron tribromide in methylene chloride).

Compound VIa, in turn, may be derived from the known compound

[Structure VII: Halo—CH₂ and Halo—CH₂ groups on benzene with two OCH₃]

Compound VII may be treated with benzylamine in an organic solvent (e.g., methylene chloride) to yield compound VI. Compound VII may be prepared as described in Wood, J. H. et al., *J. Am. Chem. Soc.* 72 (1950), 2989.

Compound V is novel and forms an integral part of this invention.

METHOD C

To prepare compound I, compound IIIA may be coupled with compound IIIB in an organic solvent (e.g., dimethylformamide) in the presence of a base (e.g., triethylamine), and a condensing agent (e.g., dicyclohexylcarbodiimide).

Compound IIIA may be derived from a compound of the formula

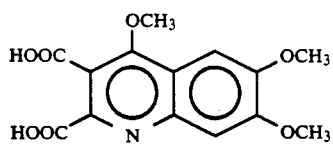

by deprotecting with, for example, boron tribromide at about −78° C., followed by hydrolysis at about room temperature.

Compound VIII may be derived from a compound of the formula

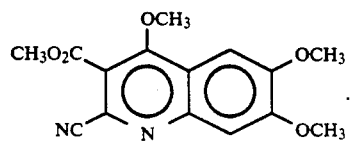

Compound IX may be treated with an alkali hydroxide (e.g., sodium hydroxide) in an organic solvent (e.g., dioxane) at. about 50° C. to yield compound VIII.

Compound IX, in turn, may be derived from a compound of the formula

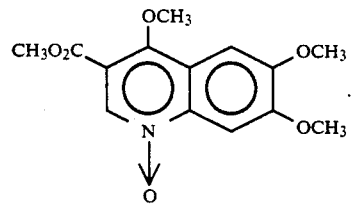

Compound X may be treated with, for example, dimethylcarbamoyl chloride and a cyanide transferring agent (e.g., trimethylsilyl cyanide) in an organic solvent (e.g., methylene chloride) to form compound IX. Compound X may be prepared as described in Example 6.

Compounds VIII, IX, and X are novel and form an integral part of this invention.

PREFERRED EMBODIMENTS OF THE INVENTION

The following working examples are preferred embodiments of the invention and are illustrative rather than limiting. Within each example, a method of preparing each intermediate compound appears below the name of the intermediate. The intermediate prepared in part A of each example will be referred to as "intermediate A" or "compound A", and so forth for intermediates prepared in parts B, C, and D, etc. Unless otherwise stated, all temperatures are given in degrees Celsius.

EXAMPLE 1

[2S-[2α,3β(Z)[[-2-[[[1-(Amino-4-thiazolyl)-2-[(2-methyl-4-oxo-1-sulfo-3-azetidinyl)amino]-2-oxoethylidene]amino]oxy]-2-methylpropanoic acid, 2-[(6,7-dihydroxy-3-quinolinyl)carbonyl]-hydrazide, monopotassium salt A. 6,7-Dimethoxy-2-methyl-3-quinolinecarboxylic acid, ethyl ester Compound A was prepared as described in W. Borsche and J. Bartenheier, *Liebigs Ann.* 548 (1941), 50.

B. 2-Formyl-6,7-Dimethoxy-3-quinolinecarboxylic is acid, ethyl ester

To a solution of compound A (25.4 g, (91.9 mmol) in 506 ml dioxane-H20 (9:), selenium dioxide (24.5 g, 220.6 mmol) was added. The mixture was heated to reflux overnight. After cooling and filtration, the solvents were distilled off in vacuo and the residue triturated with ethyl acetate to give 37.8 g of crude compound B. The crude material was purified by column chromatography on SiO$_2$-tetrahydrofuran. Yield: 13.5 g (50.6%). The crude material can also be purified by trituration with ethylacetate - saturated sodium bicarbonate solution.

Yield: 57%.
Melting point: 187.1° C.;
IR(KBr): 1700 cm$^{-1}$ (CO)
1H-NMR(TFA-d$_1$): δ=1.61(t,3H); 4.25 (s,3H); 4.28 (s,3H); 4.76 (q,2H); 7.75 (s,1H); 7.95 (s,1H); 9.59 (s,1H); 11.01 (s,1H); ppm.

C. 6,7-Dimethoxy-2,3-quinolinedicarboxylic acid, 3-ethyl ester

To a solution of compound B (2.9 g, 10.0 mmol) in 100 ml pyridine, 5.1 g (14 mmol) tetrabutylammonium permanganate was added at −10° C. The reaction was slowly warmed to room temperature. After stirring for one hour, gaseous sulfur dioxide was bubbled through the reaction mixture until decoloration. The volatiles were distilled off in vacuo, and the residue was dissolved in water. The pH was adjusted to 3.5 with half-concentrated phosphoric acid. After one night in the refrigerator, the resulting precipitate was filtered off, washed with water, and dried in vacuo to give 2.77 g (90.7%) of compound C.

Melting point: 192.1° C.
IR(KBr): 1710 cm$^{-1}$ (CO)
1H-NMR(DMSO-d$_6$): δ=1.31 (t,3H); 3.90 (s,3H); 3.95 (s,3H); 4.32 (q,2H); 7.46 (s,1H); 7.57 (s,1H); 8.68 (s,1H); ppm.

D. 6.7-Dimethoxy-3-quinolinecarboxylic acid, ethyl ester

Compound C (11.56 g, 37.9 mmol) was heated in an oil bath to 200° C. until the evolution of carbon dioxide ceased, while cooling petroleum ether was carefully added under stirring. The title compound was isolated by filtration.

Yield: 9.45 g (95.5%).
Melting point: >300° C.
IR(KBr): 1725 cm$^{-1}$ (CO).
1H-NMR(DMSO-d$_6$): δ=1.36 (t,3H); 3.90 (s,3H); 3.96 (s,3H); 4.38 (q,2H); 7.41 (s,1H); 7.52 (s,1H); 8.71 (d,1H); 9.08 (d,1H); ppm.

E. 6,7-Dimethoxy-3-quinolinecarboxylic acid

To a solution of compound D (9.13 g, 34.9 mmol) in 300 ml tetrahydrofuran was added a solution of sodium hydroxide (1.67 g, 41.9 mmol) in 300 ml water. After stirring for two days at room temperature, tetrahydrofuran was distilled off in vacuo. The pH was then adjusted to 1.5 with 3 N hydrochloric acid. The resulting precipitate was isolated by centrifugation. Yield: 4.73 g (58.1%). on concentration of the mother liquor, 3.19 g (39.2%) of compound E were obtained.

Total yield: 7.92 g (97.3%).
Melting point: >260° gas evolution.
1H-NMR(DMSO-d$_6$): δ=3.91 (s,3H); 3.94 (s,3H); 7.43 (s,1H); 7.53 (s,1H); 8.72 (d,1H); 9.09 (d, 1H); ppm.

F. 6,7-Dimethoxy-3-quinolinecarboxylic acid, 2-[(1,1-dimethyethoxy)-carbonyl]hydrazide To a solution of compound E (2.33 g, 10.0 mmol) in 40 ml dimethylformamide were added N-hydroxybenzotriazole (0.14 g, 10 mmol), dimethylaminopyridine (0.22 g, 1.0 mmol), dicyclohexylcarbodiimide (3.46 g, 13.0 mmol) and t-butyl carbazate (1.32 g, 10 mmol). After stirring overnight at room temperature, dicyclohexylurea was filtered off, and the filtrate was evaporated in vacuo. The residue was triturated with a mixture of water and ethyl acetate to give 1.54 g (44.3%) of the title compound after filtration and drying.

Melting point: 181° C.
IR(KBr): 1710, 1680 cm$^{-1}$ (CO).
1H-NMR(CMSO-d$_6$): $\delta$=1.40 (s,9H); 3.90 (s,3H); 3.92 (s,3H); 7.42 (s,2H); 8.62 (s,1H); 9.04 (s,1H); 10.41 (s,1H); ppm.

G. 6,7-Dihydroxy-3-quinolinecarboxylic acid, hydrazide, monohydrobromide

To a solution of compound F (2.57 g, 7.40 mmol) in 100 ml toluene were added at 0° C. 9.26 g (37.0 mmol) boron tribromide. The mixture was allowed to warm to room temperature and was stirred for three days. After evaporation of the solvent, the residue was triturated with a mixture of methanol and ether to give compound G after filtration and drying.

Yield: 2.26 g (quant).
Melting point: >300° C.
IR(KBr): 1695 cm$^{-1}$ (CO).
1H-NMR(DMSO-d$_6$): $\delta$=7.63 (s,2H); 9.30 (s,3H); ppm.

H. 6,7-Dihydroxy-3-quinolinecarboxylic acid, hydrazide

To a solution of compound G (3.21 g, 10.7 mmol) in 30 ml water were added 0.90 g (10.7 mmol) sodium bicarbonate. After standing overnight in the refrigerator, the resulting precipitate was filtered off, washed with water, and dried in vacuo.

Yield: 1.03 g (43.9%).
From the mother liquor, a further 0.50 g (21.3%) were isolated.
Total yield: 1.53 g (65.2%).
Melting point: >270° C.
1H-NMR(DMSO)-d$_6$): $\delta$=7.19 (s,1H); 7.27 (s,1H); 8.44 (d,1H); 8.95 (d,1H); 9.90 (s, broad, 1H); ppm.

I. [2S-[2u,3O(Z)[[-2-[[[1-(Amino-4-thiazolyl)-2-[(2-methyl-4-oxo-1-sulfo-3-azetidinyl)amino]-2-oxoethylidene]amino]oxy]-2-methylpropanoic acid, 2-[(6,7-dihydroxy-3-quinolinyl)carbonyl]-hydrazide, monopotassium salt To a solution of compound H (1.45 g, 6.61 mmol) in 40 ml dimethylformamide, N-methyl-N-trimethylsilyl trifluoracetamide (5.27 g, 26.46 mmol) was added. After stirring for 30 minutes, the solution was evaporated, and the residue dissolved in 50 ml dimethylformamide (solution (a)). To a solution of aztreonam (see U.S. Pat. No. 4,775,670) (2.88 g, 6.61 mmol) in 40 ml dimethylformamide were added tributylamine (1.23 g, 6.61 mmol), N-hydroxy-benzotriazole (0.98 g, 7.28 mmol), dimethylaminopyridine (0.08 g, 0.66 mmol) and dicyclohexylcarbodiimide (1.50 g, 7.28 mmol). After stirring for 30 minutes, the resulting dicyclohexylurea (0.80 g, 54%) was filtered off, and solution (a) was added to the filtrate. After stirring overnight at room temperature, the mixture was filtered and evaporated. The residue was taken up in acetone, filtered, and 44.6 ml of 10% potassium perfluorobutane sulfonic acid were added. The resulting crystals were filtered off (1.57 g), dissolved in water, and chromatographed on XAD-resin under medium pressure liquid chromatography (MPLC) conditions with a water:acetonitrile gradient. The sample-containing fractions were collected and freeze-dried to give 295 mg of Example 1 (6.6%).

Melting point: 235° C. dec.
IR(KBr): 1760 cm$^{-1}$.
1H-NMR(DMSO-d$_6$): $\delta$=1.82 (d,3H); 1.97 (s,3H); 2.00 (s,3H); 3.72 (dq,1H); 4.56 (dd,1H); 6.89 (s,1H); 7.45 (s,1H); 7.48 (s,1H); 9.17 (d,1H); 9.34 (d,1H); 9.60 (s,1H); 10.77 (s,1H); ppm.

EXAMPLE 2

[2S-[2$\beta$,3$\beta$(Z)]]
-2-[[[1-(2-Amino-4-thiazolyl)-2-[(2-methyl-4-oxo-1-sulfo-3-azetidinyl]amino]-2-oxoethylidene]amino]oxy]-2-methylpropanoic acid, 2-[(6,7-dihydroxy-3-isoquinolinyl)carbonyl]-hydrazide, monopotassium salt A. 1,2,3,4-Tetrahydro-6,7-dihydroxy-3-isoguinoline carboxylic acid To a solution of L-3-(3,4-dihydroxyphenyl) alanine (L-DOPA) (20 g, 101.4 mmol) in 1200 ml 0.5 N sulfuric acid were added 120 ml formaldehyde (37% weight solution in water). (L-DOPA is commercially available; e.g., Aldrich No. 216-4.) After stirring overnight at room temperature, the pH is brought between 4.0 and 4.2 with 2 N sodium hydroxide (about 260 ml) under ice cooling. A further increase of the pH causes decomposition of the product. While stirring at 3° C., the solution became turbid. To complete the crystallization, the mixture was stored in the refrigerator overnight. The crystals were collected by filtration, washed with water, and dried in vacuo.

Yield: 13.93 g (65.7%).
Melting point: 287.9°.
1H-NMR(DMSOd$_6$+TFA) $\delta$=3.10 (mc,2H); 4.20 (mc, 3H); 6.63, 6.66 (2s,2H); ppm.

B. 1,2,3,4-Tetrahydro-6,7-dihydroxy-3-isoguinolinecarboxylic acid, methyl ester, hydrochloric acid salt At 40° C., a stream of gaseous hydrochloric acid was bubbled through a solution of compound A is (32.4 g, 155.0 mmol) in 1.5 l methanol for 2 hours. After stirring overnight at room temperatuire, the solvent was distilled off in vacuo and the residue triturated with ether to furnish 38.95 g (96.8%) of the product.

Melting point: 204.8° C.
1H-NMR(DMSOd$_6$): $\delta$=3.05 (mc,2H); 3.78 (s,3H); 4.16 (s,2H); 4.45 (t,1H); 6.66 (s,2H); 10.20 (s,broad,2H); ppm.

C. 3,4-Dihydro-6,7-dihydroxy-2,3 (1H)-isoguinolinedicarboxylic acid, 3-methyl-2-(phenylmethyl) ester To a solution of compound B (30.1 g, 115.9 mmol) in 1230 ml water:tetrahydrofuran (1:1) were added benzyl chlorformate (19.8 g, 115.9 mmol) and 2 N sodium hydroxide solution dropwise to keep the PH at 8. After 2 hours, the pH was brought to 2 with 5 N hydrochloric acid. Tetrahydrofuran was distilled off in vacuo, and the aqueous phase was extracted three times with ethyl acetate. The combined organic layers were stirred with activated carbon, dried over sodium sulfate, and evaporated in vacuo to give 41.6 g (100%) of a yellow foam. IR (Film in CHCl$_3$): 1690, 1730 cm$^{-1}$ (CO). 1H-NMR(DMSOd$_6$): $\delta$=2.97 (d,2H); 3.49, 3.52 (2s,3H);

4.45 (mc,2H); 4.95 (mc,1H); 5.20 (mc,2H); 6.60 (s,2H); 7.35, 7.40 (2s,5H); 8.83 (s,2H); ppm.

D. 3,4-Dihydro-6,7-dimethoxy-2,3 (1H)-isoguinolinedicarboxylic acid, 3-methyl 2-(phenylmethyl)ester To a solution of compound C (41.2 g, 115.2 mmol) in 1680 ml water-tetrahydrofuran (1:1) were added simultaneously under ice cooling dimethylsulfate (35.36 g, 280.4 mmol) and potassium hydroxide (18.5 g (85%), 280.4 mmol) dissolved in 420 ml water.

After stirring overnight at room temperature, the pH was brought between 1 and 2 with 5 N hydrochloric acid. Tetrahydrofuran was distilled off in vacuo and the aqueous phase was extracted three times with ether. The combined organic layers were stirred with activated carbon, dried over sodium sulfate, and evaporated to give 39.4 g (88.6%) of a yellow foam.

IR(KBr): 1690, 1735 cm$^{-1}$ (CO).

1H-NMR(DMSOd$_6$): δ=3.06 (d,2H); 3.50 (m,2H); 3.66 (s,6H); 4.51 (t,2H); 5.00 (mc,1H); 5.17 (mc,2H); 6.76 (m,2H); 7.34, 7.38 (2s,5H); ppm.

E. 1,2,3,4-Tetrahydro-6,7-dimethoxy-3-isoguinolinecarboxylic acid, methyl ester

Compound D (39.4 g, 102.3 mmol), dissolved in 1300 ml N,N-dimethylformamide, was hydrogenated over 13 g palladium on activated carbon for 80 minutes. The catalyst was removed by filtration and the solvent stripped off in vacuo. Yield: 22.68 g (88.2%) of a brown oil (containing compound E and N,N-dimethylformamide). 1H-NMR(DMSO$_6$): δ=2.80 (mc,2H); 3.68 (s,9H); 3.86 (mc,2H); 6.62, 6.68 (2s,2H); ppm.

F. 6,7-Dimethoxy-3-isoguinolinecarboxylic acid, methyl ester

To a solution of compound E (19.77 g, 78.7 mmol) in 400 ml tetrahydrofuran, 2,3-dichloro-5,6-dicyano-1,4-benzoquinone (DDQ) (39.3 g, 173.1 mmol) was added. (DDQ is commercially available; e.g., Aldrich D6, 040-0.) The dark solution was heated under reflux overnight. The resulting precipitate was filtered off, dissolved in 500 ml of 1:1 methylene chloride: water, and the pH was adjusted to 10 with 1 N sodium hydroxide. The phases were separated, the aqueous phase extracted once with methylene chloride, the combined organic phases washed twice each with 100 ml of water containing a few drops of 1 N sodium hydroxide. After drying the solution and evaporating the solvent, 9.20 g (47.3%) of compound F were obtained.

Melting point: 214.9° C.

IR(KBR) 1710 cm$^{-1}$ (CO).

1H-NMR(DMSOd6+TFA): δ=4.04 (s,3H); 4.12 (s,6H); 7.82 (s,1H); 7.97 (s,1H); 8.76 (s,1H); 9.48 (s,1H); ppm.

G. 6,7-Dimethoxy-3-isoguinolinecarboxylic acid

A solution of sodium hydroxide (4.38 g, 109.4 mmol) in 70 mi water was added to a solution of compound F (22.54 g, 91.2 mmol) in 1800 ml of 1:1 water:tetrahydrofuran. After stirring overnight at room temperature, the tetrahydrofuran was distilled off in vacuo and the pH of the remaining aqueous solution was brought to 3 with 3 N hydrochloric acid. The resulting precipitate was filtered off with suction, washed with water and dried in vacuo.

Yield: 19.57 g (92.0%).

Melting point: 228.2° C.; IR(KBR) 1650 cm$^{-1}$ (CO).

1H-NMR(DMSOd$_6$): δ=3.99 (s,6H); 7.61 (2s,2H); 8.50 (s,1H); 9.18 (s,1H); 10.40 (s,very broad,1H); PPM.

H. 6,7-Dimethoxy-3-isoguinolinecarboxylic acid, 2-[(1,1-dimethylethoxy)-carbonyl]hydrazide To a solution of compound G (1.17 g, 5.0 mmol) in 20 ml dimethylformamide were added hydroxybenzotriazole (0.076 g, 0.5 mmol), dimethylaminopyridine (0.061 g, 0.5 mmol) and dicyclohexyl carbodiimide (1.34 g, 6.5 mmol). After stirring for 30 minutes, t-butyl carbazate (0.66 g, 5.0 mmol) was added, and the mixture was stirred for four days at room temperature.

Dicyclohexylurea (0.99 g, 88%) was filtered off and the filtrate was evaporated in vacuo. The residue was portioned between water and ethyl acetate. The unsoluble material was filtered off and dried to give 0.88 g (50.7%) product. The organic phase was separated, dried with sodium sulfate, and evaporated. The residue was dissolved in ether and stored overnight in the refrigerator. The resulting crystals were filtered off and dried to yield 0.55 g (31.7%) of compound H.

Total yield: 1.43 g (81.7%).

Melting point: 198.7° C.

IR 1690, 1720 cm$^{-1}$ (CO).

1H-NMR(DMSOd$_6$): δ=1.39 (s,9H); 3.91 (s,6H); 7.54 (s,1H); 7.57 (s,1H); 8.35 (s,1H); 8.89 (s,broad,1H); 9.07 (s,1H); 10.35 (s,1H); ppm.

I. 6,7-Dihydroxy-3-isoquinolinecarboxylic acid, hydrazide, monohydrobromide

Boron tribromide (2.81 g, 11.2 nunol) was added dropwise at 0° C. to a solution of compound H (0.78 g, 2.2 mmol) in 50 ml toluene. The reaction mixture was allowed to warm to room temperature and was stirred for two days. 10 ml methanol were added and after stirring for 30 minutes, the solvents were evaporated in vacuo. The residue was taken up in methanol and stirred for 2 hours. Evaporation of the methanol yielded 0.48 g (99.5%) of intermediate I.

Melting point: >300° C.

IR 1695 cm$^{-1}$ (CO).

1H-NMR(DMSO-d$_6$): δ=7.47 (s,1H); 7.64 (s,1H); 8.58 (s,1H); 9.26 (s,1H); ppm.

J. [2S-[2α,3β(Z)]]-2-[[[1-(2-Amino-4-thiazolyl)-2-[(2-methyl-4-oxo-1-sulfo-3-azetidinyl]amino]-2-oxoethylidene]amino]oxy]-2-methylpropanoic acid, 2-[(6,7-dihydroxy-3-isoquinolinyl)carbonyl]hydrazide, monopotassium salt N-methyl-N-trimethylsilyltrifluoroacetamide (1.68 g, 8.0 mmol) was added to a suspension of intermediate I (0.44 9, 2.0 mmol) in 12 ml acetonitrile. After stirring for 30 minutes, the clear, yellow solution was evaporated and the residue was taken up in 15 ml dimethylformamide (solution (a)). To a solution of aztreonam (see U.S. Pat. No. 4,775,670) (0.87 g, 2.0 mmol) in 15 ml dimethylformamide were added tributylamine (0.37 g, 2.0 mmol), hydroxybenzotriazole (0.30 g, 2.2 mmol), dimethylaminopyridine (0.024 g, 0.2 mmol) and dicyclohexylcarbodiimide (0.44 g, 2.12 mmol). After stirring for 30 minutes, the resulting dicyclohexylurea (0.26 g, 59%) was filtered off and solution (a) was added to the filtrate. After stirring overnight at room temperature, the mixture was filtered and evaporated. The residue was taken up in acetone, filtered and 13.5 ml of 10% potassium perfluorobutanesulfonic acid was added. The resulting crystals were filtered off (0.64 g), dissolved in water and chromatographed on XAD under MPLC conditions with water and 9:1 water: acetonitrile as eluents. The sample-containing fractions were collected and freeze-dried to give 120 mg of Example 2 (a yield of 8.8%).

Melting point: >225° C. (dec.).

IR 1765 cm$^{-1}$ (CO).

1H-NMR (DMSO-d$_6$): δ=1.42 (d,3H); 1.47 (s,6H); 3.71 (dd,1H); 4.53 (m,1H); 6.86 (s,1H); 7.20 (s,1H); 7.28 (s,1H); 7.30 (s,broad,1H); 8.15 (s,1H); 8.86 (s,1H); 9.32 (d,1H); ppm.

EXAMPLE 3

[2S-[2α,3<β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(6,7-dihydroxy-3-isoquinolinyl, N-oxide)-carbonyl]hydrazide, monopotassium salt A. 6,7-Dimethoxy-3-isoquinoline carboxylic acid, 2-[(1,1-dimethylethoxy)-carbonyl]hydrazide Compound A was prepared in accordance with part H of Example 2.

B. 6,7-Dimethoxy-3-isoquinolinecarboxylic acid, 2-[(1,1-dimethylethoxy)-carbonyl]hydrazide, 2-oxide To a solution of compound A (9.5 g, 27.3 mmol) in 200 ml tetrahydrofuran, m-chloroperbenzoic acid (17.7 g, 82.1 mmol) was added. The mixture was heated to reflux overnight. After cooling, compound B was isolated by filtration. The yield after drying was 6.82 g (68.7%). Melting point: 275° C. with gas evolution 1H-NMR(DMSO-d$_6$): δ=1.41 (s,9H); 3.92 (s,6H); 7.42 (s,1H); 7.65 (s,1H); 8.67 (s,1H); 8.99 (s,1H); 9.30 (s,broad,1H); 12.64 (s,1H); ppm.

C. 6,7-Dihydroxy-3-isoquinolinecarboxylic acid, hydrazide, 2-oxide, monohydrobromide To a suspension of compound B (3.63 g, 10.0 mmol) in 100 ml dry toluene, boron tribromide (12.52 g, 50.0 mmol) was added at 0° C. After stirring for three days at room temperature, methanol was added. A solution was obtained, from which the desired compound began to crystallize after a few minutes. It was filtered off, washed, and dried in vacuo to yield 1.92 g (64%) of compound C. Evaporation of the mother liquor and trituration of the residue with ether furnished another 1.05 g (35%) of compound C.

Melting point: >285° C. dec.

1H-NMR(DMSO-d$_6$): δ=7.34 (s,1H); 7.50 (s,1H); 8.63 (s,1H); 9.06 (s,1H); ppm.

D. 6,7-Dihydroxy-3-isoquinolinecarboxylic acid, 2-oxide

To a suspension of compound C (2.25 g, 7.5 mmol) in 20 ml of 1:1 water:methanol (v,v) were added 0.63 g (7.5 mmol) sodium bicarbonate. After adjusting the pH to 9 with saturated sodium bicarbonate solution, the mixture was stirred for one hour at room temperature. Compound D was filtered off, washed with water, and dried in vacuo.

Yield: 1.30 g (79.1%).
Melting point: >300° C.
IR(KBr): 1665 cm$^{-1}$ (CO).
1H-NMR(DMSO-d$_6$ +TFA): δ7.29 (s,1H); 7.43 (s,1H); 8.57 (s,1H); 9.04 (s,1H); ppm.

E. [2S-[2α,3<β(Z)]]-2-[[[1-(2-Amino-4-thiazolyl)-2-[(2-methyl-4-oxo-1-sulfo-3-azetidinyl)-amino]-2-oxoethylidene]amino]oxy]-2-methylpropanoic acid, 2-[(6,7-dihydroxy-3-isoguinolinyl, N-oxide)-carbonyl]hydrazide, monopotassium salt N-methyl-N-trimethylsilyltrifluoroacetamide (4.20 g, 21.1 mmol) was added to a suspension of compound D in 20 ml dry acetonitrile. After stirring for 30 minutes, the solution was evaporated and the residue taken up in dimethylformamide (solution (a)).

To a solution of aztreonam (2.29 g, 5.27 mmol) in 35 ml dimethylformamide were added tributylamine (0.97 g, 5.27 mmol), hydroxybenzotriazole (0.78 g, 5.79 mmol), dimethylaminopyridine (0.064 g, 0.53 mmol) and dicyclohexylcarbodiimide (1.19 g, 5.79 mmol). After stirring for 30 minutes, the resulting dicyclohexylurea (0.47 g, 40.1%) was filtered off and solution (a) was added to the filtrate. After stirring overnight at room temperature, the mixture was filtered (yielding 0.53 g, 45% of dicyclohexylurea) and evaporated. The residue was taken up in acetone, filtered, and 9.0 ml of 10% potassium perfluorobutane sulfonic acid in acetone were added. The resulting precipitate was filtered off (1.70 g), dissolved in water and chromatographed on XAD under MPLC conditions with a water - acetonitrile gradient. The sample-containing fractions were collected and freeze-dried to give 250 mg (6.9%) of Example 3.

Melting point: >220° C. dec.
IR(KBr): 1765 cm$^{-1}$ (CO).
1H-NMR(DMSO-d$_6$): δ=1.43 (d,3H); 1.48 (s,6H); 3.73 (dq,1H); 4.57 (dd,1H); 6.99 (s,1H); 7.25 (s,1H); 7.39 (s,1H); 8.56 (s,1H); 9.00 (s,1H); 9.42 (s,1H); 9.96 (s,braod,1H); ppm.

EXAMPLE 4

6,7-Dihydroxy-2-quinoxalinecarboxylic acid, [2R-[2α,3α(Z)]]-2-[[[[1-(2-amino-4-thiazolyl)-2-[(2-methyl-4-oxo-1-sulfo-3-azetidinyl)amino]-2-oxoethylidene]amino]oxy]acetyl]hydrazide A. [2R-[2α,3α(Z)]]-[[[1-(2-Amino-4-thiazolyl)-2-[(2-methyl-4-oxo-1-sulfo-3-azetidinyl)-amino]-2-oxoethylidene]amino]oxy]acetic acid Preparation of compound A is known. See, for example, United Kingdom patent application No. 2,071,650, published Sep. 23, 1981.

B. 2,2-Dimethyl-1,3-benzodioxole

A mixture of catechol (55 g, 0.5 moles), acetone (150 ml), benzene (150 ml) and p-toluenesulfonic acid (15 mg) was refluxed in a Soxlet extractor containing 140 g of baked 4Å molecular sieves for 24 hours, as described in E. R. Cole, et al., Aust. J. Chem. 33, 675 (1980). The sieves were replaced with fresh sieves and refluxing continued for another 24 hours. The solvents were removed in vacuo and the residue was triturated with 1 liter of hexane. The light yellow solution was decanted and washed with 10% NAOH until the washes were colorless. The organic layer was dried (Na$_2$SO$_4$) and evaporated to 32.4 g (43%) of title compound as an oil which was used without further purification. 1H-NMR(CDCl$_3$): δ=1.73 (s,6H); 6.78 (s,4H).

C. 2,2-Dimethyl-5-nitro-1,3-benzodioxole

A solution of 70% (conc.) nitric acid (20 ml) and glacial acetic acid (10 ml) cooled at 12° C. was treated by drops with 5 g (33.3 mmole) of compound B at a rate to maintain the temperature at 15°-20° C. Stirring was continued for 15 minutes after addition, then the brown slurry was diluted with 100 ml water and filtered. The solid was washed with water, taken up in CH$_2$Cl$_2$, dried (Na$_2$SO$_4$) and evaporated to 5.40 g (83%) of pure yellow mononitro title compound. 1H-NMR(CDCl$_3$): δ=1.73 (s,6H); 6.72 (d,1H); 7.53 (m,1H); 7.78 (m,1H).

D. 2,2-Dimethyl-5,6-dinitro-1,3-benzodioxole

A solution of 90% (fuming) nitric acid (22 ml) and glacial acetic acid (11 ml) cooled at 120C was treated in portions with solid compound C (5.4 g, <27.7 mmoles) so as to maintain the temperature of <17° C. After the addition, stirring was continued for 15 minutes, when the internal temperature began to fall. The mixture was diluted to 100 ml with water, the yellow solid filtered, washed with water, taken up in CH$_2$Cl$_2$, dried (Na$_2$-

SO4) and evaporated to give 5.43 g (82%) of pure title compound. 1H-NMR(CDCl3): δ=1.80 (s,6H); 7.17 (s,2H).

E. 5,6-Diamino-2,2-dimethyl-1,3-benzodioxole; dihydrochloride salt

A solution of compound D (2.02 g, 8.42 mmole) in 100 ml of ethyl acetate was treated with 65 mg of platinum oxide and hydrogenated for 24 hours at 1 atmosphere. The catalyst was filtered and the filtrate treated with dry HCl in ethyl acetate to give a solid. This was filtered, washed with ethyl acetate and ether, and dried in vacuo to give 2.06 g (97%) of title compound which contained solvents of crystallization (about 15% by weight).

1H-NMR(D2O); δ=1.67 (s,6H); 6.77 (s,2H).

F. 2,2-Dimethyl-1,3-dioxole[4,5 g]-quinoxaline-6,7-dicarboxylic acid

A solution of compound E (1.56 g, 6.17 mmole) in 120 ml of water was treated with NaHCO3 until pH=6.0, then treated with 1.85 g (8.19 remoles) of solid dihydroxytartaric acid, disodium salt, hydrate. The resulting slurry was stirred and heated at 75° C. for 45 minutes, giving a clear yellow solution and a small amount of amorphous brown material. The mixture was cooled to 25° C., extracted with CH2Cl2 until the organic layer was colorless, then concentrated to 30 ml at 40° C. in vacuo. This solution was acidified to pH=2.35 and the resulting thick slurry chilled and filtered. Further concentration gave a second crop, for a total of 1.47 g (82%) of title compound on drying.

1H-NMR(DMSO): δ=1.80 (s,6H); 7.40 (s,2H) 13C-NMR(DMSO): δ=25.7, 103.9, 121.6, 139.7, 143.2, 152.2, 166.2.

G. 6,7-Dihydroxyguinoxaline-2,3-dicarboxylic acid

Compound F (145 mg, 0.5 mmole) was slurried in 10 ml of concentrated HCl and heated at 75° C. for 1 hour with stirring. On initial heating, the compound dissolved, then a precipitate eventually formed. The slurry was evaporated to dryness in vacuo. The residue was initially soluble in water but formed a yellow-brown precipitate within a few minutes. The water was evaporated again and the residue was dried in vacuo for 3 hours to give the title compound as a brown solid, 125 mg.

Melting point: >300° C.

1H-NMR(DMSO): δ=7.27 (s,2H).

H. 6,7-bis(Acetyloxy)-2,3-quinoxaline dicarboxylic acid, monomethyl ester

Compound G (14.2 g, 57 mmol) and acetic anhydride (200 ml) were stirred for three hours at 80° C. After evaporation to dryness methanol (500 ml) was added and the mixture stirred at room temperature until a clear solution was obtained. The solvent was evaporated in vacuo to afford 17.1 g (86%) of compound H.

I. 6,7-bis(Acetyloxy)-2-quinoxalinecarboxylic acid, methyl ester

Compound H (17.1 g, 49 mmol) was heated in diglyme (150 ml) for two hours at 140° C. The solvent was evaporated in vacuo and the residue purified by column chromatography on silica gel. Elution with methanol afforded 9.8 g of the title compound which was further purified by trituration with ether, followed by trituration with hot ethyl acetate.

Yield: 8.23 g (55%).

J. 6,7-Dihydroxy-2-quinoxalinecarboxylic acid, hydrazide

Intermediate I (1.26 g, 4.1 mmol) and anhydrous hydrazine (0.66 g, 21 mmole) were dissolved in dry methanol (50 ml), and the mixture was heated to reflux for two hours. The solvent and excess hydrazine were evaporated in vacuo, and the residue was triturated three times with hot ether.

Yield: 0.75 g (83%).

Melting point: 197°–199° C. (dec.).

K. 6,7-Dihydroxy-2-quinoxalinecarboxylic acid, [2R-[2α,3α(Z)]]-2-[[[[1-(2-amino-4-thiazolyl)-2-[(2-methyl-4-oxo-1-sulfo-3-azetidinyl)-amino]-2-oxoethylidene]amino]oxy]acetyl]-hydrazide A solution of compound A (2.0 g, 5 mmol), tributylamine (0.93 g, 5 mmol), dicyclohexylcarbodiimide (1.13 g, 5.5 mmol), N-hydroxybenzotriazole (0.67 g, 5 mmol), and N,N-dimethylaminopyridine (20 mg) in dry dimethylsulfoxide was stirred for one hour at room temperature. A solution of compound J (1.1 g, 5 mmol) in dry dimethylsulfoxide (100 ml) was added dropwise. The mixture was stirred overnight at room temperature.

The solvent was evaporated in vacuo and the residue triturated with water. The precipitate (dicyclohexylurea) was filtered off by suction and the filtrate was adjusted to pH 6.5 by the addition of sodium bicarbonate. "Dowex 50 WX 8 (Na+)" TM was added, and the mixture was stirred for one hour at room temperature. The resin was filtered off by suction, the aqueous phase freeze-dried, and the crude product purified by MPLC on XAD using water as eluent. The product-containing fractions were freeze-dried, dissolved in water (5 ml) and adjusted to pH 2.5 by the addition of hydrochloric acid. The precipitate was filtered off by suction and dried in vacuo.

Yield: 0.33 g (11%).

This material was combined with 0.15 g of another batch and further purified by a MPLC on XAD.

Yield: 0.07 g (1.6%)

Melting point: slow dec. >230° C.

EXAMPLE 5

[2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(1,4-dihydro-6,7-dihydroxy-4-oxo-3-quinolinyl)carbonyl]-hydrazide, monopotassium salt A. 1,4-Dihydro-6,7-dimethoxy-4-oxo-3-quinolinecarboxylic acid Preparation of compound A is described in B. Riegel et al., *J. Am. Chem. Soc.* 68 (1946), p. 1264.

B. 1,4-Dihydro-6,7-dimethoxy-4-oxo-3-quinolinecarboxylic acid, 2-[(1,1-dimethylethoxy)carbonyl]hydrazide To a solution of compound A (3.0 g, 12.0 mmol) in 200 ml dry dimethylformamide, triethylamine (2.43 g, 24.0 mmol) was added at −2° C. After the dropwise addition of diphenylphosphorylchloride (3.22 g, 12.0 mmol), the mixture was stirred for 5 hours at 0° C. A solution of t-butyl carbazate (1.59 g, 12.0 mmol) in 30 ml dimethylformamide was added, and the mixture was stirred at room temperature overnight. The solvent was distilled off i.11 vacuo, and the residue was triturated with 200 ml ethyl acetate and 200 ml water. The insoluble product (compound B) was filtered off with suction, washed with ether, and dried in vacuo.

Yield: 2.0 g (46%).

Melting point: >300° C.

IR(KBr): 1665, 1715 cm$^{-1}$ (CO).

1H-NMR(DMSOd6): δ=1.40 (s,9H); 3.88, 3.89 (2s,6H); 7.12 (s,1H); 7.57 (s,1H); 8.62 (s,1H); 8.95

(s,broad,1H); 11.29 (s,broad,1H); 12.57 (s,very broad,1H); ppm.

C. 1,4-Dihydro-6,7-dihydroxy-4-oxo-3-quinolinecarboxylic acid, hydrazide, monohydrobromide At −67° C., compound B (1.82 g, 5 mmol) was added to a solution of boron tribromide (7.5 g, 30 mmol) in 170 ml methylene chloride in portions. The mixture was allowed to warm to room temperature overnight and was then stirred for an additional three days. The resulting solid (3.56 g) was filtered off and stirred for 24 hours in 30 ml methanol containing one drop of hydrochloric acid in methanol. The product was filtered off with suction, washed with methanol, and dried in vacuo.

Yield: 1.19 g (100%).
Melting point: >300° C.
1H-NMR(DMSOd$_6$): $\delta$=7.08 (s,1H); 7.51 (s,1H); 8.55 (d,1H); 12.05 (s,1H); 1/1.78 (d,1H); ppm.

D. [2S-[2$\alpha$,3$\beta$(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(1,4-dihydro-6,7-dihydroxy-4-oxo-3-quinolinyl)carbonyl]-hydrazide, monopotassium salt Aztreonam (535 mg, 1.0 mmol) in 4 ml of dry dimethylformamide under argon at 25° C. was treated with:
(1) tributylamine (185 mg, 1 mmol) in 0.5 ml dimethylformamide,
(2) hydroxybenzotriazole (20 mg, 0.13 mmol) in water,
(3) dimethylaminopyridine (10 mg, 0.08 mmol) and
(4) dicyclohexyl carbodiimide (206 mg, 1.0 mmole) in 2 ml of dimethylformamide.

The mixture was stirred at 25° C. for 15 minutes, at which time a precipitate formed and the solution began to turn yellow. A slurry of compound C (235 mg, 1.0 mmol) in a total of 3 ml of dimethylformamide was added, and the resulting slurry (pH 4.5) was stirred at 250C for 16 hours. The mixture was then filtered, and the filtrate evaporated in vacuo to a gum.

This gum was dissolved in a mixture of acetonitrile and water, and the pH (3.85) adjusted to 6.10 with potassium bicarbonate. This solution was passed through "Dowex AG50 (K$^+$)" TM, and the eluent was adjusted to pH 2.0 with dilute hydrochloric acid. The organics were evaporated in vacuo and the resulting slurry applied to a 75-ml HP-20 column and eluted with 200 ml of water before starting a steep (3:2) acetonitrile:water gradient. Product fractions were combined and lyophilized to give 220 mg of crude all-white powder. This material gave a gum with water and dissolved when the pH was raised to 6.1 with potassium bicarbonate. Chromatography on 75 ml of HP-20 in water followed by a shallow (1:2) acetonitrile: water gradient and lyophilization of pure product fractions gave Example 5 as a white solid. The yield was 56 mg (8.1%).

IR(KBr): 1761 cm$^{-1}$ (CO).
1H-NMR(D$_2$O): $\delta$=1.54 (d,3H); 1.58 (s,6H); 4.24 (m,1H); (4.60, d,1H; burried in H$_2$O at 4.65); 6.68 (s,1H); 6.99 (s,1H); 7.29 (s,1H); 8.38 (s,1H).

EXAMPLE 6

[2S-[2$\alpha$,3$\beta$(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(1,4-dihydro-1,6,7-trihydroxy-4-oxo-3-quinolinyl)carbonyl]-hydrazide, monopotassium salt A. 1,4-Dihydro-6,7-dimethoxy-4-oxo-3-quinolinecarboxylic acid, ethyl esters Preparation of compound A is described in B. Riegel et al., *J. Am. Chem. Soc.* 68 (1946), p. 1264.

B. 4-Chloro-6,7-dimethoxy-3-quinolinecarboxyl..4.c acid, ethyl ester 43 ml dimethylformamide were added to a suspension of compound A (60.0 g, 216 mmol) in 800 ml thionylchloride. A clear solution was obtained and the temperature rose to 40° C. After stirring overnight at room temperature, the volatiles were distilled off in vacuo and 1 liter of ice water was added to the residue. The resulting precipitate was filtered off, washed with water and dried in vacuo at 70° C.

Yield: 50.9 g (79.7%).
Melting point: 161.6° C.
IR(KBr): 1730 cm$^{-1}$ (CO).
1H-NMR(DMSO-d$_6$): $\delta$=1.30 (t,3H); 3.92 (s,3H); 4.02 (s,3H); 4.28 (q,2H); 7.46 (s,1H); 8.42 (s,1H); 8.99 (s,1H); ppm.

C. 4,6,7-Trimethoxy-3-quinolinecarboxylic acid, methyl ester

A solution of sodium methoxide prepared from 7.89 g (342.8 mmol) sodium and 500 ml methanol was added to a solution of compound B (50.7 g, 171.4 mmol) in 2500 ml tetrahydrofuran. After stirring overnight at room temperature, the solvents were distilled off in vacuo and the residue triturated with water. The yield of compound C after drying was 37.4 g (78.7%).

Melting point: 139.5° C.
IR(KBr): 1725 cm$^{-1}$ (CO).
1H-NMR(DMSO-d$_6$): $\delta$=3.90 (s,3H); 3.94 (s,3H); 3.95 (s,3H); 4.04 (s,3H); 7.40 (s,1H); 7.42 (s,1H); 8.86 (s,1H); ppm.

D. 4,6,7-Trimethoxy-3-quinolinecarboxylic acid, methyl ester, 1-oxide

To a filtered solution of compound C (18.0 g, 65.0 mmol) in 420 ml of tetrahydrofuran, m-chloroperbenzoic acid (36.4 g, 255 mmol) was added. The mixture was heated to reflux overnight. After standing for another night in the refrigerator, the resulting crystals were filtered off, washed with tetrahydrofuran, and dried in vacuo.

Yield: 14.4 g (75.5%).
Melting point: 190.9° C.
IR(KBr): 1700 cm$^{-1}$ (CO).
1H-NMR(DMSO-d$_6$): $\delta$=3.90 (s,3H); 3.99 (s,3H); 4.00 (s,3H); 4.02 (s,3H); 7.35 (s,1H); 7.90 (s,1H); 8.59 (s,1H); ppm.

E. 4,6,7-Trimethoxy-3-quinolinecarboxylic acid, 1-oxide 136 ml of 2.5 N sodium hydroxide solution were added to a solution of compound D (8.8 g, 30.0 mmol) in 380 ml of methanol. After stirring overnight at room temperature, the pH was adjusted to 2 with 3 N hydrochloric acid. The resulting precipitate was filtered, washed with water, and dried in vacuo.

Yield: 7.6 g (90.7%).
Melting point: >162° C. dec.
IR(KBr): 1715 cm$^{-1}$ (CO).
1H-NMR(TFA-d$_1$): $\delta$=4.18 (s,3H); 4.24 (s,3H); 4.50 (s,3H); 7.88 (s,1H); 7.91 (s,1H); 9.44 (s,1H); ppm.

F. 4,6,7-Trimethoxy-3-quinolinecarboxylic acid, 2-[(1,1-dimethylethoxy)carbonyl]hydrazide, 1-oxide Compound E (7.50 g, 27.8 mmol), hydroxybenzotriazole (3.63 g, 26.8 mmol) and dimethylaminopyridine (0.33 g, 2.7 mmol) in 490 ml dimethylformamide were heated to 70° C. until a clear solution was obtained. At 30° C., dicyclohexylcarbodiimide (5.54 g, 26.8 mmol) was added. After stirring for 2 hours, t-butyl carbazate (3.55 g, 26.8 mmole) dissolved in 60 ml dry dimethylformamide was added dropwise. After stirring overnight at room temperature, the resulting dicyclohexylurea was filtered off (3.7 g) and the filtrate was evaporated in vacuo. The residue was triturated with 300 ml ethyl acetate, filtered, and dried in vacuo.

Yield: 7.8 g (74%).
Melting point: 190.3' C.
IR(KBr): 1700, 1740 cm$^{-1}$ (CO).
1H-NMR(DMSO-d$_6$): δ=1.41 (s,9H); 3.94 (s,3H); 3.95 (s,3H); 4.05 (S,3H); 7.38 (s,1H); 7.85 (s,1H); 8.21 (s,1H); 9.09 (s,broad,1H); 10.29 (s,broad,1H); ppm.

G. 1,4-Dihydro-1,6,7-trihydroxy-4-oxo-3-quinolinecarboxylic acid, hydrazide

To a suspension of compound F (7.71 g, 19.6 mmol) in 550 ml dry toluene were added at 0° C. 29.5 g (117.8 mmol) boron tribromide. After stirring for two days at room temperature, methanol was added under ice-bath cooling. The mixture was evaporated and the residue triturated with 100 ml of a methanol solution containing 0.5 ml of 3 N hydrochloric acid. The hydrobromide salt was filtered off (3.62 g, 55.6%), dissolved in 100 ml water:methanol (1:1, v/v), and 900 mg sodium bicarbonate were added. After evaporation of the methanol, compound G was filtered off, washed with water, and dried in vacuo.

Yield: 2.67 g (41%).
Melting point: >300° C.
1H-NMR(DMSO-d$_6$): δ=7.19 (s,1H); 7.56 (s,1H); 8.56 (s,1H); 11.05 (s,broad,1H); ppm.

H. [2S-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[(1,4-dihydro-1,6,7-trihydroxy-4-oxo-3-quinolinyl)carbonyl]hydrazide, monopotassium salt N-methyl-N-trimethylsilyltrifluoroacetamide (8.57 g, 43.0 mmol) (MSTFA) was added to a suspension of compound G (2.15 g, 8,6 mmol) in 60 ml dry acetonitrile. (MSTFA is commercially available, e.g., Aldrich 24,210.1.) After stirring for 30 minutes, the resulting solution was evaporated and the residue dissolved in 20 ml dimethylformamide (solution (a)).

To a solution of aztreonam (3.74 g, 8.6 mmol) in 70 ml dimethylformamide were added tributylamine (1.58 q, 8.6 mmol), hydroxybenzotriazole (1.17 g, 8.6 mmol), dimethylaminopyridine (0.10 g, 0.86 mmol), dicyclohexylcarbodiimide (2.32 g, 11.12 mmol) and finally solution (a). After stirring overnight at room temperature, dicyclohexylurea was filtered off and the filtrate was evaporated in vacuo. The residue was taken up in acetone, filtered, and 16 ml of 10% potassium perfluorobutane sulfonic acid in acetone were added. The resulting crystals were filtered off (2.09 g), dissolved in water, and chromatographed on XAD with a water:acetonitrile gradient. The sample-containing fractions were collected and freeze-dried to give 350 mg of Example 6, which were again chromatographed on "Organogen" with a water:acetonitrile gradient. Yield: 140 mg (2.3%).

Melting point: >300° C.
IR(KBr): 1760 cm$^{-1}$ (CO).
1H-NMR(DMSO-d$_6$+TFA): δ=1.41 (d,3H); 1.48 (s,6H); 3.75 (dq,1H); 4.57 (d,1H); 7.14 (s,1H); 7.22 (s,1H); 7.59 (s,1H); 8,68 (s,1H); ppm.

EXAMPLE 7

[2R-[2α,3β(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[[1-(carboxymethyl)-1,4-dihydro-6,7-dihydroxy-4-oxo-3-quinolinyl]carbonyl]hydrazide, dipotassium salt A. 1,2-Bis(phenylmethoxy)benzene To a solution of 1,2-dihydroxybenzene (60 g, 0.54 mol) in 240 ml acetone, potassium carbonate (220 g, 1.59 mol) was added. After heating to reflux, benzylbromide (256.6 g, 1.5 mol) was added dropwise. The mixture was heated to reflux overnight, cooled, and poured onto 1 liter ice-water. The resulting precipitate (compound A) was filtered off with suction, washed with water, and dried in vacuo.

Yield: 143.50 g, (91.5%).
Melting point: 57°-59° C.
1H-NMR(DMSO-d$_6$): δ=5.11 (s,4H); 6.80-7.15 (m,4H); 7.25-7.60 (m,10H); ppm.

B. 3,4-Bis(phenylmethoxy)nitrobenzene

To a suspension of compound A (26 g, 89.5 mmol) in 120 ml acetic acid, 24 ml of 65% nitric acid in 120 ml acetic acid was added dropwise. From the resulting solution, compound B crystallized on stirring. 50 ml acetic acid were added to improve stirring. After one hour, the mixture was poured onto 1 liter ice-water. The solid was filtered off with suction, washed with water and recrystallized from 500 ml ethanol.

Yield: 27.15 g (90.5%).
Melting point: 95°-97° C.
IR(KBr): 1350, 1510 cm$^{-1}$ (NO$_2$). 1H-NMR(DMSO-d$_6$): δ=5.26 (s,2H); 5.30 (s,2H); 7.20-7.60 (m,11H); 7.80-8.00 (m,2H); ppm.

C. 3,4-Bis(phenylmethoxy)benzeneamine

To a boiling solution of compound B (72.15 g, 215.2 mmol) in 1030 ml ethanol was added a hot solution of sodium sulfide nonahydrate (106.0 g, 430.4 mmol) in 140 ml water:ethanol (1:1,v/v). After the addition, the mixture was heated to reflux for 35 minutes and then cooled. The resulting precipitate (compound C) was filtered off, washed with water, and dried in vacuo.

Yield: 52.6 g (80%).
Melting point: 109°-111° C.
IR(KBr): 3360, 3430 cm$^{-1}$ (NH$_2$).
1H-NMR(DMSO-d$_6$): δ4.73 (s,broad,2H); 4.93 (s,2H); 5.04 (s,2H); 6.10 (dd,AB,1H); 6.38 (d,1H); 6.73 (d,AB,1H); 7.20-7.60 (m,10H); ppm.

D. [[[3,4-Bis(phenylmethoxy)phenyl]amino]methylene]propanedioic acid

To a solution of compound C (52.6 g, 172.2 mmol) in 315 ml dimethylformamide, diethyl ethoxymethylenemalonate (42.8 g, 198.0 mmol) was added. After stirring for three days at room temperature, the solvent was distilled off in vacuo and the residue was triturated with water to give 86.7 g (quant.) of compound D.

Melting point: 73°-76° C.
IR(KBr): 1700 cm$^{-1}$ (CO).
1H-NMR(DMSO-d$_6$): δ=1.26, 1.27 (2t,611); 4.13, 4.20 (2q,4H); 5.12 (s,2H); 5.18 (s,2H); 6.88 (dd,AB,1H); 7.06 (d,AB,1H); 7.22 (d,1H); 7.25-7.60 (m,10H); 8.32 (d,1H); 10.71 (d,1H); PPM.

E. 1,4-Dihydro-4-oxo-6,7-bis(phenylmethoxy)-3-quinoline carboxylic acid, ethyl ester Compound D (2.55 g, 5.36 mmol) was added under stirring to 21 ml boiling diphenylether. The mixture was heated to reflux for 15 minutes while the resulting ethanol was distilled off. After cooling, ether was added to the resulting suspension. The precipitate (compound E) was filtered off and dried in vacuo.

Yield: 160 g (70%).
Melting point: 291° C.

IR(KBr): 1795 cm$^{-1}$ (CO).

1H-NMR(TFA): δ=1.49 (s,3H); 4.61 (q,2H); 5.33 (s,4H); 7.20–7.50 (m,10H); 7.58 (s,1H); 7.98 (s,1H); 9.02 (s,1H); ppm.

F. 1,4-Dihydro-4-oxo-6,7-bis(phenylmethoxy)-3-quinoline carboxylic acid

To a solution of 9.0 g (0.16 mmol) potassium hydroxide in 240 ml ethanol (80%), 17.0 g (0.04 mmol) of compound E were added and the mixture was stirred at 80° C. for 20 hours. The solvent was removed in vacuo, and the residue was taken up in 300 ml water. The desired acid (compound F) was precipitated by slow addition of 2 N hydrochloric acid, collected by suction, washed with water and ethanol, and dried in vacuo over phosphorus pentoxide.

Yield: 13.5 g (84%);

Melting point: 271°–272° C. (dec.).

G. 1,4-Dihydro-4-oxo-6,7-bis(phenylmethoxy)-3-quinoline carboxylic acid, 2-[(phenylmethoxy)carbonyl]hydrazide To a cold (0° C.) suspension of 13.2 g (33 mmol) of compound F in 900 ml dry dimethylformamide, 6.6 g (66 mmol) triethylamine were added, followed by slow addition of 8.9 g (33 mmol) diphenyl chlorophosphate. After stirring at 0° C. for 6 hours, a solution of 5.5 g (33 mmol) benzyl carbazate in 50 ml dry dimethylformamide were slowly added. Stirring was continued overnight at 0° C. The solvent was removed from the clear solution (0.1 Torr) to leave an oily residue which was taken up in a mixture of 250 ml water and 250 ml ethyl acetate, and stirring was continued until a solid was precipitated. After addition of 150 ml more of ethyl acetate, the precipitate was collected by suction, successively washed with water, ethyl acetate and ether, and dried in vacuo over phosphorus pentoxide.

Yield: 10.8 g (60%).

Melting point: (sint 151° C.) 231°–234° C.

H. 4-Oxo-6,7-bis(phenylmethoxy)-3-[[2-[[phenylmethoxy)carbonyl]hydrazino]carbonyl]-1-(4H)-quinolineacetic acid, phenylmethylester To a solution of 8.2 g (15 mmol) of compound G in 100 ml dry dimethylformamide, 2.8 g (20 mmol) potassium carbonate and 5.0 g (18 mmol) iodoacetic acid, phenylmethylester were added. The mixture was stirred at 75° C. for 3.5 hours. After cooling and filtration, the filtrate was evaporated in vacuo to leave a residue that was dissolved in a mixture of 150 ml ethyl acetate and 59 ml water. The organic layer was separated, washed with water and brine, and dried over sodium sulfate. After evaporation of the solvent in vacuo, the residue was solidified by stirring with 80 ml methanol for 30 minutes. The precipitate was filtered off and successively washed with methanol, ether and n-pentane.

Yield: 6.7 g (64%).

Melting point: 168°–170° C.

I. 3-(Hydrazinocarbonyl)-6,7-dihydroxy-4-oxo-1(4H)-quinoline acetic acid 1.4 g (2.0 mmol) of compound H were dissolved in 20 ml dry dimethylformamide. After the addition of 1.99 g (10 mmol) N-methyl-N-trimethylsilyl-trifluoroacetamide, the mixture was hydrogenated at room temperature in the presence of 0.5 g palladium (10%) carbon; the hydrogenation was complete after 90 minutes. After removal of the catalyst by filtration, the filtrate was evaporated in vacuo and the residue was stirred with 25 ml methanol for 15 minutes. The solid (intermediate I) was collected by suction, washed with methanol and ether, and dried in vacuo over phosphorus pentoxide.

Yield: 0.35 g (60%).

Melting point: dec. >300° C.

J. [2R-[2u,3u(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, 2-[[1-(carboxymethyl)-1,4-dihydro-6,7-dihydroxy-4-oxo-3-quinolinyl]carbonyl]-hydrazide, dipotassium salt Part J used a zwitterion of β-methylaztreonam, [2R-[2α,3α(Z)]]-3-[[(2-amino-4-thiazolyl)-[(1-carboxy-1-methylethoxy)imino]acetyl]amino]-2-methyl-4-oxo-1-azetidinesulfonic acid, potassium salt (1:2). This compound may be prepared by procedures described in U.S. Pat. No. 4,775,670.

This part also used persilylated intermediate I. The persilylated intermediate I was prepared by (1) stirring 0.88 g (3.0 mmol) intermediate I in 25 ml acetonitrile containing 3.0 g (15 mmol) N-methyl-N-trimethylsilyl trifluoroacetamide for one hour at room temperature, (2) evaporating in vacuo, and (3) redissolving the residue in 30 ml dry dimethylformamide.

A stirred solution of 1.3 g (3.0 mmol) of β-methyl-aztreonam was mixed with:

(1) 1.06 g (3.0 mmol) trioctylamine, (2) 0.49 g (3.3 mmol) N-hydroxybenzotriazole, (3) 0.036 g (0.3 mmol) 4-dimethylaminopyridine in 30 ml dry dimethylformamide, and (4) 0.68 g (3.3 mmol) dicyclohexylcarbodiimide.

Stirring was continued for 2.5 hours at room temperature. Then a solution of 3 mmol of persilylated intermediate I in 30 ml dry dimethylformamide was added, and the mixture was stirred for 48 hours at room temperature. After filtration of a side product (dicyclohexylurea) and evaporation in vacuo, the residue was stirred in 35 ml methanol for 20 minutes and the solvent was removed in vacuo. The oily residue was redissolved in 50 ml acetone, filtered again to remove dicyclohexylurea, and mixed with 25 ml of a 10% solution of potassium perfluorobutane sulfonic acid in acetone. The precipitated salt was collected by suction, washed with acetone, ether and n-pentane, and dried in vacuo.

The crude material (2.2 g) was dissolved in 15 ml water at pH 5.5 (adjusted by addition of a few drops of dilute potassium hydroxide) and then chromatographed (MPLC) on XAD-2 resin eluting with water/acetonitrile (2.5%). Freeze-drying of the appropriate fractions gave 0.4 g (17%) of Example 7 with a purity of 90 to 96% (by high pressure liquid chromatography) and additional 0.4 g (17%) of Example 7 with a purity of 98% (by high pressure liquid chromatography).

Melting point: dec. >225° C.

EXAMPLES 8a and 8b

8a:
1,4-Dihydro-6,7-dihydroxy-4-oxo-2,3-quinolinedicarboxylic acid,
3-[[2R-[2α,3β(Z)]]-2-[2-[[[1-(2-amino-4-thiazolyl)-2-[(2-methyl-4-oxo-1-sulfo-3-azetidinyl)amino]-2-oxoethylidene]amino]oxy-2-methyl-1-oxopropyl]-hydrazide], disodium salt 8b:
1,4-Dihydro-6,7-dihydroxy-4-oxo-2,3-quinolinedicarboxylic acid,
2-[[2R-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methyl-1-oxopropyl]hydrazide], disodium salt A. 4,6,7-Trimethoxy-3-quinolinecarboxylic acid, methyl ester, 1-oxide Compound A was prepared as described in Example 6, parts A to E.

B. 2-Cyano-4,6,7-trimethoxy-3-quinolinecarboxylic acid, methyl ester

To a solution of compound A (4.81 g, 16.4 mmol) in 100 ml methylene chloride, dimethylcarbamoyl chloride (1.76 g, 16.4 mmol) was added. Thereafter, trimethylsilyl cyanide (1.95 g, 19.68 mmol) was added dropwise. After stirring for 5 days at room temperature, 10 ml saturated sodium chloride solution was added, and the mixture was stirred for another hour. The phases were separated, the organic phase washed twice with water and evaporated after drying. The residue was triturated with ether to give 4.47 g (90.1%) of compound B.

Melting point: 174°-178° C.
IR: 2235 cm$^{-1}$ (CN); 1710 cm$^{-1}$ (CO).
$^1$NMR(DMSO-d$_6$): δ=3.95 (s,3H); 3.96 (s,3H); 3.99 (s,3H); 4.06 (s,3H); 7.39 (s,1H); 7.47 (s,1H); ppm.

C. 4,6,7-Trimethoxy-2,3-quinolinedicarboxylic acid

To a solution of compound B (11.92 g, 39.4 mmol) in 400 ml dioxane were added 197 ml 1 N sodium hydroxide solution, and the mixture was stirred for 28 hours at 50° C. Dioxane was distilled off in vacuo., water was added and the pH was brought to 1 with hydrochloric acid. After standing overnight in the refrigerator, the precipitate (compound C) was filtered off, washed with water, and dried in vacuo.

Yield: 9.35 g (77.2%).
Melting point: >160° C. dec.
IR(KBR) 1710 cm$^{-1}$ (CO).
1H-NMR(DMSO-d$_6$): δ=3.99 (s,6H); 4.06 (s,3H); 7.38 (s,1H); 7.50 (s,1H); ppm.

D. 1,4-Dihydro-6,7-dihydroxy-4-oxo-2,3-quinolinedicarboxylic acid

At <78° C,, a solution of compound C (10.0 g, 30.0 mmol) in 225 ml methylene chloride was mixed with 45 g (180.0 mmol) boron tribromide. The mixture was allowed to warm to room temperature overnight and was stirred for another 5 days at room temperature. The mixture was hydrolyzed by adding 20 ml water. The solvents were distilled off in vacuo, and the residue was suspended in 250 ml water and then freeze-dried. The crude material (27.18 g) was suspended in water and the pH was adjusted to 6.0 with 3 N sodium hydroxide. The resulting solution was chromatographed on HP20 with water as eluent. The product-containing fractions were combined, and the pH was brought to 2.0 with hydrochloric acid. The resulting acid was filtered off, washed with water, and dried in vacuo.

Yield: 9.5 g (purity 90.8%).
The chromatographic purification was repeated on XAD to give 5.07 g (63%) of the title compound. (purity 93.6%).
Melting point: 288°-290° C.
1H-NMR(DMSOd$_6$): δ=7.11 (s,1H); 7.49 (s,1H); ppm.

E. 2-[(1,3-Dihydro-1,3-dioxo-2H-isoindol-2-yl)-oxy]-2-methylpropanoic acid

A cold solution of the known compound 2-[(1,3-dihydro-1,3-dioxo-2H-isoindol-2-yl)oxy]-2-methyl-propionate, diphenylmethyl ester (20.8 g, 0.05 mol) in dry dichloromethane (90 ml) was dropped into a solution of anisole (8 ml) in trifluoroacetic acid (80 ml) at −10° C. The mixture was stirred for 1 hour at 0° C. and then evaporated in vacuo to leave a residue which was solidified by stirring with dry ether. The precipitate was collected by suction, washed with few ml dry ether and dried in vacuo.

Melting point: 134° C.
Yield: 8.4 g (67.50%).

F. 2-[(1,3-Dihydro-1,3-dioxo-2H-isoindol-2-yl)-oxy]-3-methoxylpropanoyl chloride A solution of compound E (56.5 g, 227.0 mmol) in 150 ml thionylchloride was heated to 65° C. for 5 hours. The thionylchloride was distilled off and the residue triturated with petroleum ether.

Yield: 55.36 g (91.1%).
Melting point: 65°-68° C.
1R(KBr): 1740, 1780, 1840 cm$^{-1}$ (CO).
1H-NMR(DMSO-d$_6$): δ=1.50 (s,6H); 7.93 (s,4H); ppm.

G. 2-[(1,3-Dihydro-1,3-dioxo-2H-isoindol-2-yl)-oxy]-2-methylpropanoic acid, 2-[(1,1-dimethylethoxy)carbonyl]hydrazide To a solution of compound F (26.76 g, 0.10 mol) and dimethylaminopyridine (24 mg, 0.2 mmol) in 220 ml dry tetrahydrofuran was added dropwise at 0° C. a solution of tertbutylcarbazate (13.21 g, 0.10 mol) and triethylamine (13.8 g, 0.136 mol) in 110 ml abs. tetrahydrofuran. The mixture was stirred overnight, filtered and evaporated. The residue was partitioned between water and ethylacetate, the phases were separated and the organic phase washed with 0.5 N hydrochloric acid and saturated sodium hydrogen carbonate solution. Drying and evaporation furnished 35.1 g (96.6%) of compound G.

Melting Point: 50°-55° C.
IR(KBr): 1735, 1795, cm$^{-1}$ (Co).
1H-NMR(DMSO-d$_6$): δ=1.38 (s,9H); 1.49 (s,6H); 7.91 (s,4H); 8.80 (s,broad,1H); 9.70 (s,broad); ppm.

H. 2-(Aminooxy)-2-methylpropanoic acid, 2-[(1,1-dimethylethoxy)carbonyl]hydrazide Hydrazine (9.64 g, 192.6 mmol) was added to a solution of compound G (35.0 g, 96.3 mmol) in 360 ml dichloromethane at 0° C. After stirring for 2 hours the resulting precipitate was filtered off and the filtrate evaporated to give 5.38 g (23.9%) of the title compound. The precipitate was is triturated with 500 ml tetrahydrofuran, filtered and evaporated to give another 16.2 g (72.1%) of the title compound H. Total yield 21.58 g (96.0%).

Melting point: 130°-135° C.
1H-NMR(DMSO-d$_6$): δ=1.25 (s,6H); 1.40 (s,9H); 5.82 (s,2H); 8.70 (s,broad,1H); 9.38 (s,broad,1H); PPM.

I. (Z)-Amino-u-[[2-[2-[(1,1-dimethylethoxy)-carbonyl]hydrazino]-1,1-dimethyl-2-oxoethoxy]-imino]-4-thiazoleacetic acid A solution of compound H (7.0 g, 30 mmol) and 2-amino-u-oxo-4-thiazoleacetic acid (5.16 g, 30 mmol) in 300 ml dry dimethylformamide was stirred for three days at room temperature. The solvent was distilled off and the residue dissolved in water by the addition of sodium hydrogen carbonate. The solution was extracted twice with ethylacetate and the pH adjusted to 2 with 3 N hydrochloric acid. The resulting precipitate was filtered off and the filtrate stored overnight in the refrigerator. The title compound I was filtered off and dried in vacuo.

Yield: 1.58 g (13.6%). Evaporation of the filtrate yielded a second crop with 4.74 g (40.8%).

Total yield: 6.32 g (54.4%).

Melting point: 197° C.

IR(KBr): 1670, 1730 cm$^{-1}$ (CO).

1H-NMR(DMSO-d$_6$): $\delta$=1.36 (s,9H); 1.41 (s,6H); 6.90 (s,1H); 7.31 (s,broad,2H); 8.77 (s,1H); 8.91 (s,1H); ppm.

J. [2R-[2u,3u(Z)]]-2-[[[1-(2-Amino-4-thiazolyl)-2-[(2-methyl-41-oxo-1-sulfo-3-azetidinyl)-amino]-2-oxoethylidene]amino]oxy]-2-methylpropanoic acid, 2-[(1,1-dimethylethoxy)carbonyl]hydrazide, monopotassium salt To a solution of (2R-cis)-3-Amino-2-methyl-4-oxo-1-azetidinesulfonic acid (4.5 g, 25.0 mmol) in 50 ml dimethylformamide tributylamine (4.63 g, 25.0 mmol) was added and stirred for 30 minutes (solution A). To a solution of intermediate I (9.69 g, 25.0 mmol) in 250 ml dimethylformamide were added N-hydroxybenzotriazole (3.38 g, 25.0 mmol), dimethylaminopyridine (0.3 g, 2.5 mmol), dicyclohexylcarbodiimide (5.67 g, 27.5 mmol) and after 30 minutes of stirring solution A. The mixture was stirred overnight at room temperature, filtered and evaporated. The residue was dissolved in acetone and potassium perfluorobutan sulfonic acid (8.87 g, 26.0 mmol) was added. The resulting precipitate was filtered off with suction, washed with acetone and dried to give 17.78 g (quant.) of the crude title compound J.

IR(KBr): 1760 cm$^{-1}$ (CO).

1H-NMR(DMSO-d$_6$): $\delta$=1.1-1.6 (m,18H); 4.04 (dq,1H); 5.08 (dd,1H); 6.80 (s,1H); 7.21 (s,broad,2H); 8.78 (s,broad,1H); 9.15 (s,broad,1H); 9.32 (d,1H); ppm.

K. [2R-[2$\alpha$,3$\alpha$(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid, hydrazide, monosodium salt compound J (17.7 g, 25 mmol) was added at 0° C. to a mixture of 18 ml anisole and 90 ml trifluoroacetic acid. After stirring for 1 hour ether was added and the resulting TFA-salt was filtered off with suction. This salt was suspended in water, the pH was adjusted to 6.5 with sodium hydroxide solution to give a solution which was freeze dried. Yield of crude title compound K was 19.38 g, 8 grams thereof were chromatographed in two portions on XAD resin under MPLC conditions with water as eluent. Yield of pure title compound K 2.27 g (46.8% from compound I).

Melting point: >200° C. sinters, >240° C. dec.

IR(KBr): 1760 cm$^{-1}$ (CO).

1H-NMR(DMSO-d$_6$): $\delta$=1.22 (d,3H); 1.32 (s,3H); 1.39 (s,3H); 4.02 (dq,1H); 4.25 (s,broad,2H); 5.08 (dd,1H); 6.78 (s,1H); 7.30 (s,broad,2H); 8.68 (s,1H); 9.42 (d,1H); ppm.

L. Examples 8a and 8b

A solution of compound D (0.74 g, 2.78 mmol) and dicyclohexyl carbodiimide (0.66 g, 3.2 mmol) in 20 ml dimethylformamide was stirred for 2 hours. A solution of compound K (1.18 g, 2.5 mmol) and triethylamine (0.28 g, 2.78 mmol) in 20 ml dimethylformamide, pre-stirred for 1 hour, was added. After stirring overnight at room temperature, dicyclohexylurea was filtered off and the solvent was removed in vacuo. The residue was suspended in water and freeze-dried after the pH had been adjusted to 6. The crude compound (2.39 g) was chromatographed on XAD with a water-acetonitrile gradient. The product was eluted with water, yielding 238 mg (13.1%), purity 96.1% of Example 8a and 145 mg (purity 49.5% +23%) of Example 8b.

Example 8b was eluted as the triethylamine salt with 10% acetonitrile, yielding 297 mg (16.3%), purity 83.4% and 223 mg (purity 63.2%). The two fractions containing Example 8b were combined and chromatographed again, but Example 8b was not obtained with a higher purity since it decomposed during the chromatography to give the starting material (compound K).

Melting point of Example 8a: >270° C. sinters.

IR(KBr): 1760 cm$^{-1}$ (CO).

1H-NMR(DMSO-d$_6$): $\delta$=1.27 (d,3H); 1.42 (s,6H); 4.05 (dq,1H); 5.11 (dd,1H); 6.82 (s,1H); 7.03 (s,1H); 7.39 (s,broad,2H); 7.45 (s,1H); 9.42 (d,1H); 9.47 (s,broad,1H); 12.12 (s,broad,2H); ppm.

EXAMPLE 9

(2S-trans)-1,4-Dihydro-6,7-dihydroxy-4-oxo-3-cinnolinecarboxylic acid, 2-[[2-[[[1-(2-amino-4-thiazolyl)-2-[(2-methyl-4-oxo-1-sulfo-3-azetidinyl)amino]-2-oxoethylidene]amino]oxy]-2-methyl-1-oxopropyl]hydrazide, monopotassium salt A. 1,4-Dihydro-4-oxo-[1,3]-dioxolo[4,5-g]cinnoline-3-carboxylic acid Preparation of compound A is described in K. Schofield and I. C. E. Simpson, J. Chem. Soc. (1945), 512.

B. 1,4-Dihydro-4-oxo-[1,3]-dioxolo[4,5-g]cinnoline-3-carboxylic acid, 2-[(1,1-dimethylethoxy)carbonyl]hydrazide(11)

To a solution of compound A (0.59 g, 2.52 mmol) in 20 ml dimethylformamide were added hydroxybenzotriazole (0.034 g, 0.25 mmol), dimethylaminopyridine (0.018 g, 0.15 mmol) and dicyclohexylcarbodiimide (0.67 g, 3.28 mmol). After stirring for 30 minutes, t-butylcarbazate (0.33 g, 2.52 mmol) was added and the mixture was stirred for 48 hours at room temperature. Dicyclohexylurea was filtered off, and the filtrate was evaporated in vacuo. The residue was triturated with boiling methanol, and after cooling, filtered and dried in vacuo.

Yield: 0.58 g (66.1,).

IR(KBr): 1670, 1725 cm$^{-1}$ (CO).

1H-NMR(DMSO-d$_6$): $\delta$=1.41 (s,9H); 6.26 (s,2H); 7.10 (s,1H); 7.42 (s,1H); 9.12 (s,broad,1H); 11.08 (s,broad,1H); PPM.

C. 1,4-Dihydro-6,7-dihydroxy-4-oxo-3-cinnolinecarboxylic acid hydrazide

Boron tribromide (2.62 g, 10.45 mmol) was added dropwise at −78° C. to a suspension of compound B (0.52 g, 1.49 mmol) in 15 ml methylene chloride. The reaction mixture was allowed to warm to room temperature and was stirred for 3 days. 15 ml methanol were added with cooling to is 0° C. The resulting solution was evaporated n vacuo, the residue taken up in methanol containing three drops of concentrated hydrochloric acid and stirred for 3 hours. After evaporation, the residual hydrobromic acid salt (0.69 g) was suspended in water and its PH was adjusted to 7.3 with sodium bicarbonate. Filtration and drying furnished 0.28 g (79.5%) of compound C.

Melting point: >300° C.
IR(KBr): 1760 cm$^{-1}$ (CO).
1H-NMR(DMSO-d$_6$+TFA): δ7.12 (s,1H); 7.46 (s,1H); ppm.

D. (2S-trans)-1,4-Dihydro-6,7-dihydroxy-4-oxo-3-cinnolinecarboxylic acid, 2-[[2-[[[1-(2-amino-4-thiazolyl)-2-[(2-methyl-4-oxo-1-sulfo-3-azetidinyl)amino]-2-oxoethylidene]amino]oxy]-2-methyl-1-oxopropyl]hydrazide, monopotassium salt N-methyl-N-trimethylsilyl-trifluoroacetamide (0.78 g, 3.88 mmol) was added to a suspension of compound C (0.23 g, 0.97 mmol) in 8 ml acetonitrile. After stirring for 30 minutes at 40° C., the clear solution was evaporated and the residue was taken up in 10 ml dimethylformamide (solution (a)).

To a solution of aztreonam (0.34 g, 0.78 mmol) in 10 ml dimethylformamide were added tributylamine (0.144 g, 0.78 mmol) and after ten minutes of stirring, hydroxybenzotriazole (0.10 g, 0.78 mmol), dimethylaminopyridine (10 mg, 0.078 mmol) and dicyclohexylcarbodiimide (0.19 g, 0.93 mmol). After stirring for one hour, solution (a) was added.

The mixture was stirred overnight at room temperature. The solvent was distilled off in vacuo and the residue was triturated with 30 ml acetone. After filtration, the insoluble material was suspended in water:acetone (2:1, v/v) and the pH was brought to 6 with dilute potassium hydroxide solution. After filtration, the filtrate was freeze-dried to give 335 mg of crude Example 9.

This crude product was dissolved in water and passed through a short ion exchange resin column ("Dowex (K+)" ™). The eluate was concentrated and chromatographed on "Organogen" ™ under MPLC-conditions with water as eluent. The sample-containing fractions were freeze-dried to give 100 mg (18.5%) of Example 9.

Melting point: >300° C.
IR(KBr): 1760 cm$^{-1}$ (CO).
1H-NMR(DMSO-d$_6$): δ=1.42 (d,3H); 1.44 (s,6H); 3.72 (dq,1H); 4.56 (dd,1H); 6.85 (s,1H); 7.06 (s,1H); 7.38 (s,broad,2H); 7.46 (s,1H); 9.32 (d,1H); 9.75 (s,broad,1H); 10.40 (s,broad,1H); 10.95 (s,broad,1H); 11.73 (s,broad,1H); ppm.

EXAMPLE 10

(2S-trans)-5,6-Dihydroxy-2-benzofurancarboxylic is acid, 2-[2-[[[1-(2-amino-4-thiazolyl)-2-[(2-methyl-4-oxo-1-sulfo-3-azetidinyl)amino]-2-oxo-ethylidene]amino]oxy]-2-methyl-1-oxopropyl]-hydrazide, monopotassium salt A. 5,6-Dimethoxy-benzofurancarboxylic acid The preparation of compound A is described in G. Singh, G. V., Nair and K. P. Aggarwal, *J. Sci. Ind. Research* (India) 15B, (1956), 190 (C. A. 51 416i).

B. 5,6-Dimethoxy-2-benzofurnacarboxylic acid, 2-[(1,1-dimethylethoxy)-carbonyl]hydrazide At −10° C., a solution of compound A (0.89 g, 4.0 mmol) in 20 ml dimethylformamide was mixed with triethylamine (1.62 g, 16.0 mmol) and diphenyl chlorophosphate (1.07 g, 4.0 mmol). After stirring for 4 hours, t-butylcarbazate (0.53 g, 4.0 mmol) was added and the mixture was stirred overnight.

The solvent was evaporated and the residue partitioned between ethyl acetate and water. The phases were separated, the organic phase washed with water and brine and dried over sodium sulfate. After filtration and evaporation, 1.43 g of the desired compound B were obtained.

Melting point: 77°-80° C.
IR(KBr): 1730, 1675 cm$^{-1}$ (CO).
1H-NMR(DMSO-d$_6$): δ=1.41 (s,9H); 3.80 (s,3H); 3.83 (s,3H); 7.25 (s,3H); 7.52 (s,1H); 8.95 (s,1H); 10.28 (s,1H); ppm.

C. 5,6-Dihydroxy-2-benzofurancarboxylic acid, hydrazide

To a solution of compound B (1.36 g, 4.0 mmol) in 50 ml methylene chloride, boron tribromide (4.0 g, 16.0 mmol) was added at −78° C. The mixture was allowed to warm to room temperature and was stirred overnight. 100 ml methanol were added dropwise at 0° C. and after stirring for 30 minutes, the volatiles were distilled off in vacuo.

The residue was dissolved in 200 ml methanol and activated carbon, and one drop of concentrated hydrochloric acid was added. After stirring for three hours, the mixture was filtered and evaporated, and the residue was triturated with ether to give 1.11 g of the hydrobromide of compound C. The salt was dissolved in water, one equivalent of sodium bicarbonate was added, and the resulting precipitate was filtered off and dried in vacuo.

Yield: 0.53 g (63.7%).
Melting point: 280°-285° C.
IR(KBr): 1665 cm$^{-1}$ (CO).
1H-NMR(DMSO-d$_6$): δ=6.90 (s,1H); 6.92 (s,1H); 7.29 (s,1H); 9.25 (s,broad,2H); 9.70 (s,broad,1H); PPM.

D. (2S-trans)-5,6-Dihydroxy-2-benzofurancarboxylic acid, 2-[2-[[[1-(2-amino-4-thiazolyl)-2-[(2-methyl-4-oxo-1-sulfo-3-azetidinyl)amino]-2-oxo-ethylidene]amino]oxy]-2-methyl-1-oxopropyl]hydrazide, monopotassium salt N-methyl-N-trimethylsilyl-trifluoroacetamide (2.34 g, 11.8 mmol) was added to a suspension of compound C (0.49 g, 2.35 mmol) in 15 ml dry acetonitrile. After stirring for 30 minutes, the solution was evaporated and the residue was dissolved in 10 ml dry diethylformamide (solution (a)).

To a solution of aztreonam (1.02 g, 2.35 mmol) in 20 ml dimethylformamide were added tributylamine (0.44 g, 2.35 mmol) and after stirring for ten minutes, hydroxybenzotriazole (0.32 g, 2.35 mmol), dimethylaminopyridine (29 mg, 0.23 mmol) and dicyclohexylcarbodiimide (0.63 g, 3.06 mmol). After stirring for 1 hour, solution (a) was added and the mixture was stirred overnight at room temperature. Dicyclohexylurea was filtered off, and the filtrate was evaporated in vacuo. Added to the residue were acetone and, after filtration, 4 ml of 10% potassium perflorobutane sulfonic acid in acetone. The resulting precipitate was filtered off (yielding 0.91 g), dissolved in water, and chromatographed on "Organogen" ™ under MPLC conditions with water as eluent. The sample-containing fractions were combined and freeze-dried to give 350 mg (22.4%) of Example 10.

Melting point: >240° C. sinters.
IR(KBr): 1760 cm$^{-1}$ (CO).
1H-NMR(DMSO-d$_6$): δ=1.43 (d,3H); 1.44 (s,3H); 1.46 (s,3H); 3.71 (dq,1H); 4.56 (dd,1H); 6.86 (s,1H); 6.96 (s,1H); 7.00 (s,1H); 7.30 (s,broad,2H); 7.43 (s,1H); 9.12

(s,broad,1H); 9.31 (d,1H); 9.42 (s,1H); 9.55 (s,broad,1H); 10.33 (s,1H); ppm.

EXAMPLE 11

[2R-(2α,3α(Z)]-2-[2-[2-[2-[[[1-(2-Amino-4-thiazolyl)--2-[(2-methyl-4-oxo-1-sulfo-3-azetidinyl)amino]-2-oxoethylidene]amino]oxy]-2-methyl-1-oxopropyl]hydrazino]-2-oxoethyl]-2,3-dihydro-5,6-dihydroxy-2-methyl-1H-isoindolium, inner salt A. 1,2-bis(Chloromethyl)-4,5-dimethoxybenzene
Compound A was prepared as described in J. H. Wood et al., *J. Am. Chem. Soc.* 72 (1950), p. 2989.

B. 2,3-Dihydro-5,6-dimethoxy-2-(phenylmethyl)-1H-isoindole

Benzylamine (53.6 g, 0.5 mmol) was added to a solution of compound A (23.5 g, 0.1 mmol) in 500 ml methylene chloride. The mixture was stirred for 48 hours. The resulting crystals were filtered off with suction and purified by column chromatography on silica gel using ethyl acetate as eluent.

Yield: 15.8 g (58.7%).
Melting point: 108°-110° C.
1H-NMR(DMSO-d$_6$): δ=3,68 (s,6H); 3.77 (s,4H); 3.82 (s,2H); 6.83 (s,2H); 7.32 (mc, 5H); ppm. C. 2,3-Dihydro-5,6-dimethoxy-2-methyl-2-(phenylmethyl)-1H-isoindolium iodide (4)

Methyliodide (8.52 g, 60.0 mmol) was added to a solution of compound B (5.39 g, 20.0 mmol) in 500 ml ether. After stirring for 70 hours at room temperature, the resulting crystals (compound C) were filtered off and dried in vacuo.

Yield: 6.71 g (81.6%).
From the filtrate, a second crop of the desired compound C was isolated: 1.07 g (13%).
Total yield: 7.78 g (94.6%).
Melting point: 135°-138° C.
1H-NMR(DMSO-d$_6$): δ=3.08 (s,3H); 3.75 (s,6H); 4.59 (d,AB,2H); 4.85 (s,2H); 5.04 (d,AB,2H); 7.08 (s,2H); 7.55 (mc,5H); ppm.

D. 2,3-Dihydro-5,6-dimethoxy-2-methyl-1H-isoindole hydroiodide

Compound C (6.65 g, 16.17 mmol), dissolved in 200 ml dimethylformamide containing 2 g 20% palladium hydroxide on carbon, was hydrogenated at 50° C. and 3 bar overnight. The solvent was removed in vacuo and the residue was triturated with ether to give 4.53 g (87.3%) of compound D.

Melting point: 185°-190° C.
1H-NMR(DMSO-d$_6$): δ=3.02 (s,3H); 3.74 (s,6H); 4.51 (s,4H); 7.04 (s,2H); 10.50 (s,very broad,1H); PPM.

E. 2,3-Dihydro-5,6-dimethoxy-2-methyl-1H-isoindole 13.7 ml of 1 N sodium hydroxide solution were added to a solution of compound D (4.4 g, 3.7 mmol) in 180 ml water:ethyl acetate (1:1,v/v). The phases were separated after stirring for 5 minutes, the aqueous phase washed twice with ethyl acetate, and the combined organic phases washed with water and brine. Drying and evaporating gave 1.86 g (7C.3%) of the desired compound E.

Melting point: 70° C.
1H-NMR(DMSO-d$_6$): δ=2.50 (s,3H); 3.76 (s,6H); 3.78 (s,4H); 6.90 (s,2H); ppm.

F. Bromoacetic acid, 2-[(1,1-dimethylethoxy)carbonyl]hydrazide

To a solution of t-butyl carbazate (66.08 g, 0.50 mol) and triethylamine (50.51 g, 0.50 mmol) in 1000 ml ethylacetate was added dropwise at 0° C. a solution of bromoacetyl bromide (100.93 g, 0.50 mol) in 1000 ml ethylacetate. After stirring overnight at −5° C., the ammonium salts were filtered off, the filtrate was washed with diluted hydrochloric acid and water, dried and evaporated. The residue was triturated with ether and petroleum ether to give a total of 05.0 g, (89.3%) of compound F.

Melting point: 100° to 105° C.
IR(KBr): 1670, 1725 cm$^{-1}$ (co).
1H-NMR(DMSO-d$_6$): δ=1.38 (s,9H); 3.84 (s,2H); 8.90 (s,1H); 9.97 (s,1H); ppm.

G. Iodoacetic acid, 2-[(1,1-dimethylethoxy)carbonyl]hydrazide

Sodium iodide (3.0 g, 20.0 mmol) were added to a solution of compound F (2.35 g, 10.0 mmol) in 60 ml acetone, and the mixture was stirred overnight at room temperature. The solids were filtered off and partitioned between water and ethylacetate. The organic phase was separated, washed with water and brine and dried over sodium sulfate. Evaporation yielded 2.36 g (83.6%) of is compound G.

IR(KBr): 1675, 1720 cm$^{-1}$ (CO).
1H-NMR(DMSO-d$_6$): δ=1.37 (s,9H); 3.58 (s,2H); 3.82 (s,1H); 9.86 (s,1H); ppm.

H. 2-[2-[2-[(1,1-Dimethylethoxy)carbonyl]hydrazino]-2-oxoethyl]-2,3-dihydro-5,6-dimethoxy-2-methyl-1H-isoindolium iodide A solution of compound G (2.02 g, 7.14 mmol) in 50 ml ether:tetrahydrofuran (2:1,v/v) was added to a solution of compound E in 50 ml ether: tetrahydrofuran (2:1,v/v). After stirring overnight at room temperature, the resulting precipitate was filtered off with suction and dried in vacuo.

Yield: 3.15 g (94.8%).
Melting point: >140° C. dec.
IR(KBr): 1695, 1740 cm$^{-1}$ (CO).
1H-NMR(DMSO-d$_6$): δ=1.42 (s,9H); 3.38 (s,3H); 3.78 (s,6H); 4.51 (s,2H); 4,88 (d,AB,2H); 4.98 (d,AB,2H); 7.12 (s,2H); 9.11 (s,broad,1H); 10.33 (s,1H); ppm.

I. 2-(2-Hydrazino-2-oxoethyl)-2,3-dihydro-5,6-dihydroxy-2-methyl-1H-isoindolium bromide, monohydrobromide Boron tribromide (6.11 g, 24.4 mmol) was added dropwise at −78° C. to a solution of compound H (3.02 g, 6.1 mmol) in 40 ml methylene chloride. After stirring for 3 days at room temperature, 20 ml of methanol were added. The resulting precipitate (intermediate I) was filtered off with suction and dried in vacuo.

Yield: 1.99 g (81.5%).
For further purification, the material was chromatographed on XAD with water as eluent.
Yield of pure intermediate I was 1.08 g (44.5%).
Melting point: 90°-110° C.
IR(KBr): 1710, 1730 cm$^{-1}$ (CO).
1H-NMR(DMSO-d$_6$): δ=3.27 (s,3H); 4.67 (s,2H); 4.81 (2AB,4H); 6.82 (s,2H); ppm.

J. [2R-(2α,3α(Z)]-2-[2-[2-[2-[[[1-(2-Amino-4-thiazolyl)-2-[(2-methyl-4-oxo-1-sulfo-3-azetidinyl)amino]-2-oxoethylidene]amino]oxy]-2-methyl-1-oxopropyl]hydrazino]-2-oxoethyl]-2, 3-dihydro-5,6-dihydroxy-2-methyl-1H-isoindolium, inner salt Tributylamine (0.49 g, 2.62 mmol) was added to a solution of intermediate 1 (1.05 g, 2.62 mmol) in 10 ml dry dimethylformamide. The mixture was stirred for 30 minutes to give a suspension (suspension (a)).

To a solution of 4-β-methylaztreonam (1.14 g, 2.62 mmol; see Example 7, part J) in 30 ml dry dimethylformamide were added tributylamine (0.49 g, 2.62 mmol) and, after stirring for ten minutes, hydroxybenzotriazole (0.35 g, 2.62 mmol), dimethylaminopyridine (32 mg, 0.26 mmol) and dicyclohexylcarbodiimide (0.6 g, 2.88 mmol). The mixture was stirred for 30 minutes and then added to suspension (a). (For preparation of 4-β-methyl aztreonam, see U.S. Pat. No. 4,775,670).

After stirring overnight at room temperature and concentrating to a third of the original volume, dicyclohexylurea was filtered., off. The solvent was removed totally in vacuo; the residue, triturated with acetone, filtered and dried in vacuo (2.11 g). The resulting crude Example 11 was purified by column chromatography on XAD under MPLC conditions using a water-acetonitrile gradient. The sample-containing fractions were collected and freeze-dried to give 230 mg (13.4%) of Example 11 with a purity of 96.5% and 520 mg (30.3%) of Example 11 with a purity of 41.5%. The latter was chromatographed a second time on XAD to give 110 mg (6.4%) of Example 11 with a purity of 98.2%.

Melting point: 242°–270° C. dec.
IR(KBr): 1760 cm$^{-1}$ (CO).
1H-NMR(DMSO-d$_6$+TFA): δ=1.25 (d,3H); 1.49 (s,3H); 1.50 (s,3H); 3.26 (s,3H); 4.10 (q,1H); 4.45 (s,2H); 4.72 (d,AB,2H); 4.82 (d,AB,2H); 5.18 (d,1H); 6.80 (s,2H); 7.11 (S,1H); ppm.

EXAMPLE 12

[2R-[2α,3α(Z)]]-2-[[[1-(2-Amino-4-thiazolyl)-2-[(2-methyl-4-oxo-1-sulfo-3-azetidinyl)amino]-2-oxoethylidene]amino]oxy]-2-methylpropanoic acid 2-[(1,3-dihydro-5,6-dihydroxy-2H-isoindol-2-yl)

A. 2,3-Dihydro-5,6-dimethoxy-2-(phenylmethyl)-1H-isoindole

Compound A was prepared as described in Example 11, part B.

B. 2-[2-[2-[(1,1-Dimethylethoxy)carbonyl]-hydrazino]-2-oxoethyl]-2,3-dihydro-5,6-dimethoxy-2-(phenylmethyl)-1H-isoindolium bromide A solution of compound A (3.55 g, 13.18 mmol), and bromoacetic acid, 2-[(1,1-dimethylethoxy)-carbonyl]-hydrazide (3.1 g, 13.18 mmol; see Example 11, part F) in 360 ml ether were heated to reflux for 3 days. The resulting precipitate was filtered off with suction and dried in vacuo.

Yield: 3.59 g (52.2%).
Melting point: 186°–187° C.
IR(KBr): 1700, 1740 cm$^{-1}$ (CO).
1H-NMR(DMSO-d$_6$): δ=1.42 (s,9H); 3.76 (s,6H); 4.28 (s,2H); 4.82 (s,2H); 4.92 (d,AB,2H); 5.12 (d,AB,2H); 7.06 (S,2H); 7.51 (mc,5H); 9.15 (s,1H); 10.40 (s,1H); ppm.

C. 1,3-Dihydro-5,6-dimethoxy-2H-isoindole-2-acetic acid, 2-[(1,1-dimethylethoxy)carbonyl]hydrazide, monohydrobromide At 50° C., hydrogen was bubbled for 3 hours through a solution of compound B (2.18 g, 4.17 mmol) in 100 ml dimethylformamide containing 1 g 10% palladium on carbon. The catalyst was filtered off and the solvent evaporated n vacuo. The residue was dissolved in water and freeze-dried to give 1.97 g (quant.) of compound C.

Melting point: 171°–180° C.
IR(KBr): 1675, 1720 cm$^{-1}$ (CO).

1H-NMR(DMSO-d$_6$): δ=1.41 (s,9H); 3.74 (s,6H); 4.34 (s,2H); 4.60 (s,4H); 7.05 (s,2H); 9.08 (s,1H); 10.26 (s,1H); ppm.

D. 1,3-Dihydro-5,6-dihydroxy-2H-isoindole-2-acetic acid, hydrazide, dihydrobromide To a suspension of compound C (0.78 g, 1.80 mmol) in 30 ml dry methylene chloride was added at −78° C. boron tribromide (2.25 g, 9.0 mmol). The mixture was stirred overnight at room temperature. Upon the addition of 10 ml methanol at 0° C., a precipitate was formed which was filtered off with suction and dried in vacuo.

Yield: 0.45 g (64.8%).
Melting point: 155°–180° C.
IR(KBr): 1725 cm$^{-1}$ (CO).
1H-NMR(DMSO-d$_6$): δ=4.45 (s,2H); 4.54 (s,broad,4H); 6.78 (S,2H); ppm.

E. [2R-[2u,3u(Z)]1-2-[[[J-(2-Amino-4-thiazolyl)-2-[(2-methyl-4-oxo-1-sulfo-3-azetidinyl)amino]-2-oxoethylidene]amino]oxyl-2-methylpropanoic acid, 2-[(1,3-dihydro-5,6-dihydroxy-2H-isoindol-2-yl)acetyl]hydrazide To a solution of 4-β-methylaztreonam (see U.S. Pat. No. 4,775,670) (0.46 g, 1.05 mmol) in 15 ml dimethylformamide were added tributylamine (0.14 g, 1.05 mmol), hydroxybenzotriazole (0.14 g, 1.05 mmol), dimethylaminopyridine (12 mg, 0.1 mmol) and dicyclohexylcarbodiimide (0.24 g, 1.15 mmol). After stirring for one hour, tributylamine (0.28 g, 2.1 mmol) and finally compound D (0.40 g, 1.05 mmol) were added.

The mixture was stirred overnight at room temperature, and the resulting dicyclohexylurea was filtered off. The solvent was evaporated in vacuo and the residue triturated with acetone to give 0.67 g of crude Example 12. This material was suspended in 100 ml water, the pH brought to 6.5 with sodium hydroxide solution, and after filtration of impurities, the pH was adjusted to 5.0. Freeze-drying of the solution furnished 0.51 g of Example 12, which were purified by column chromatography on XAD under MPLC conditions with water:acetonitrile gradient. The sample-containing fractions were combined and freeze-dried to give 233 mg (34.6%) of Example 12.

Melting point: >220° C. dec.
IR(KBr): 1760 cm$^{-1}$ (CO).
1H-NMR(DMSO-d$_6$): δ=1 27 (d,3H); 1.43 (s,3H); 1.47 (s,3H); 4.06 (dq,1H); 4.14, 4.32 (2s,broad,4H); 4.65, 4.70 (2s,broad,2H); 5.10 (dd,1H); 6.72, 6.75 (2s,1H); 6.85, 6.88 (2s,1H); 7.30 (s,broad,2H); 9.18 (s,2H); 9.31 (d,1H); 9.40, 9.75 (2s,1H); 10.04, 0.46 (2s,1H); 10.82, 10.98 (2s,broad,1H); ppm. Mixture of zwitterions (AMT-H+; isoindole-H+).

What is claimed is:
1. A compound having the formula

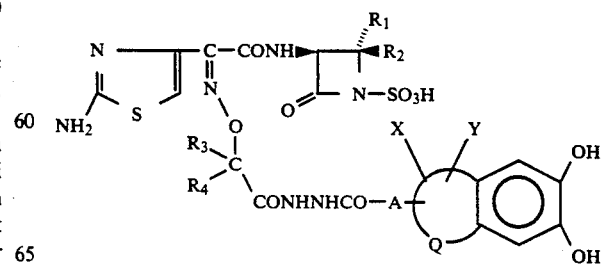

and pharmaceutically acceptable salts thereof, wherein
A is a bond or alkylene of 1 to 10 carbon atoms;

Q completes a 5- or 6-membered heterocyclic ring having one or two heteroatoms selected from nitrogen, $NR_5$, $\oplus NR_6$, sulfur, or oxygen;

X is optionally present and is attached to an available carbon atom in the heterocyclic ring and is hydrogen or oxo;

Y is attached to an available carbon atom in the heterocyclic ring and is hydrogen, amino, hydroxy, halogen, carboxamide, nitride or carboxyl, provided that Y is not carboxyl when

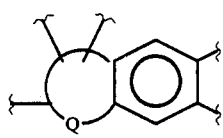

is 2-quinolyl, 3-quinolyl, or quinoxalyl;

$R_1$ and $R_2$ are the same or different and each is independently hydrogen, alkyl, alkenyl, alkynyl, cycloalkyl, phenyl, substituted phenyl, or $R_7$; or one of $R_1$ and $R_2$ is hydrogen and the other is azide, halomethyl, dihalomethyl, trihalomethyl, alkoxycarbonyl, 2-phenlethenyl, 2-phenylethynyl, carboxy, $-CH_2X_1$, $-S-X_2$, $O-X_2$, or

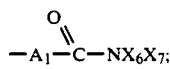

$R_3$ and $R_4$ are the same or different and each is hydrogen or alkyl or $R_3$ and $R_4$ together with the carbon atom to which they are attached are cycloalkyl;

$R_5$ is hydrogen, lower alkyl, cycloalkyl, hydroxyl, amino, oxide or carboxyalkyl;

$R_6$ is hydrogen, lower alkyl, cycloalkyl, or carboxyalkyl;

$R_7$ is a 4, 5, 6, or 7-membered heterocycle;

$X_1$ is azido, amino, hydroxyl,

alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

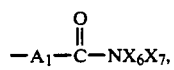

$-S-X_2$, or $-O-X_2$;

$X_2$ is alkyl, substituted alkyl, phenyl, substituted phenyl, phenylalkyl, (substituted phenyl)alkyl, alkanoyl, substituted alkanoyl, phenylalkanoyl, (substituted phenyl)alkanoyl, phenylcarbonyl, (substituted phenyl)carbonyl, or heteroarylcarbonyl; and when $X_1$ is $O-X_2$, then $X_2$ can also be alkylideneamino, alkanoylamino, carboxylakylideneamino, alkylsulfonylamino, alkoxycarbonyl-alkylsulfonylamino

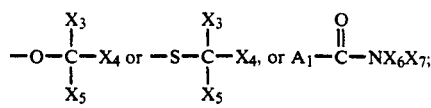

one of $X_3$ and $X_4$ is hydrogen and the other is hydrogen or alkyl; or $X_3$ and $X_4$, taken together with the carbon atom to which they are attached, form a cycloalkyl group;

$X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano.

$X_6$ and $X_7$ are the same or different and each is hydrogen, alkyl, phenyl or substituted phenyl; or $X_6$ is hydrogen and $X_7$ is amino, substituted amino, alkanoylamino or alkoxy; or $X_6$ and $X_7$, taken together with the nitrogen atom to which they are attached, form a 4, 5, 6 or 7-membered heterocycle;

$A_1$ is $-CH=CH-$, $-(CH_2)_m-$, $-(CH_2)_m-O-$, $-(CH_2)_m-NH-$, or $-CH_2S-CH_2-$; and m is 0, 1, or 2; and wherein "substituted alkyl" refers to alkyl groups substituted with one or more azido, amino, halogen, hydroxyl, carboxyl, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkylsulfinyl, or alkylsulfonyl groups;

"substituted phenyl" refers to phenyl groups substituted with 1, 2, or 3 amino, halogen, hydroxy, trifluoromethyl, alkyl (of 1 to 4 carbon atoms), alkoxy (of 1 to 4 carbon atoms), alkanoyloxy, aminocarbonyl, or carboxyl groups;

"substituted amino" refers to a group having the formula $-NX_8X_9$ wherein $X_8$ is hydrogen, alkyl, phenyl, substituted phenyl, phenylalkyl, or (substituted phenyl)alkyl, and $X_9$ is alkyl, phenyl, substituted phenyl, phenylalkyl, (substituted phenyl)alkyl, hydroxyl, cyano, alkoxy, phenylalkoxy, or amino; and "a 4, 5, 6 or 7-membered heterocycle" refers to saturated and unsaturated, aromatic and nonaromatic rings having one to four nitrogen atoms and/or 1 or 2 oxygen or sulfur atoms in the ring, which maybe substituted with oxo, halogen, hydroxyl, nitro, amino, cyano, trifluoromethyl, alkyl of 1 to 4 carbons, alkoxy of 1 to 4 carbons, alkylsulfonyl, phenyl, substituted phenyl, 2-furfurylideneamino, benzylideneamino, or substituted alkyl groups.

2. The compound according to claim 1 wherein $R_1$ is hydrogen or alkyl.

3. The compound according to claim 1 wherein $R_2$ is hydrogen or alkyl.

4. The compound according to claim 1, wherein one of $R_1$ and $R_2$ is hydrogen and the other is alkyl.

5. The compound according to claim 1 wherein $R_3$ is hydrogen or alkyl.

6. The compound according to claim 1 wherein $R_4$ is hydrogen or alkyl.

7. The compound according to claim 1 wherein $R_3$ and $R_4$ are both hydrogen or both alkyl.

8. The compound according to claim 1 wherein Y is hydrogen, hydroxyl or carboxyl.

9. The compound according to claim 1 wherein one of the heteroatoms in the heterocyclic ring defined by Q is $NR_5$ or $NR_6\oplus$ wherein $R_5$ is hydrogen, alkyl, carboxyalkyl, oxide or hydroxyl and $R_6$ is methyl, or carboxyalkyl.

10. The compound according to claim 1 wherein the heteroatoms in the heterocyclic ring defined by Q are one or two nitrogen atoms or one oxygen or one sulfur atom.

11. The compound according to claim 1 wherein

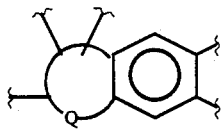

is quinolyl, isoquinolyl, quinoxalyl, cinnolyl, benzofuranyl, isoindolyl, isoindolium, dihydroisoindolyl, or dihydroisoindolium.

12. The compound according to claim 1, [2S-[2α,3β(Z)[[-2-[[[1-(2-amino-4-thiazolyl)-2-[(2-methyl-4-oxo-1-sulfo-3-azetidinyl)amino]-2-oxoethyl-diene]amino]oxy]-2-methylpropanoic acid, 2-[(6,7-dihydroxy-3-quinolinyl)carbonyl]hydrazide, monopotassium salt;

[2S-8    2α,3β(Z)]]-2-[[[1-(2-amino-4-thiazolyl)-2-[(2-methyl-4-oxo-1-sulfo-3-azetidinyl]amino]-2-oxoethylidene]amino]oxy]-2-methylpropanoic acid, 2-[(6,7-dihydroxy-3-isoquinolinyl)carbonyl]hydrazide, monopotassium salt;

[2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 2-[(6,7-dihydroxy-3-isoquinolinyl, N-oxide)carbonyl]hydrazide, monopotassium salt;

6,7-dihydroxy-2-quinoxalinecarboxylic acid, [2R-[2α,3α(Z)]]-2-[[[[1-(2-amino-4-thiazolyl)-2-[(2-methyl-4-oxo-1-sulfo-3-azetidinyl)amino]-2-oxoethylidene]amino]oxy]acetyl]hydrazide;

[2S-[2α,3β(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 2-[(1,4-dihydro-6,7-dihydroxy-4-oxo-3-quinolinyl)carbonyl]hydrazide, monopotassium salt;

[2S-[2α,3β(Z)]]-2-[[[1-(2-amino-4-thiazolyl)-2-[(2-methyl-4-oxo-1-sulfo-3-azetidinyl)amino]-2-oxoethyl-diene]amino]oxy]-2-methylpropanoic acid, 2-[(1,4-dihydro-1,6,7-trihydroxy-4-oxo-3-quinolinyl)carbonyl]hydrazide, monopotassium salt;

[2R-[2α,3α(Z)]]-2-[[[1-(2-amino-4-thiazolyl)-2-[(2-methyl-4-oxo-1-sulfo-3-azetidinyl)amino]-2-oxoethyl-diene]amino]oxy]-2-methylpropanoic acid, 2-[[1-(carboxymethyl)-1,4-dihydro-6,7-dihydroxy-4-oxo-3-quinolinyl]carbonyl]hydrazide, dipotassium salt;

1,4-dihydro-6,7-dihydroxy-4-oxo-2,3-quinolinedicarboxylic acid, 3-[[2R-[2α,3α(Z)]]-2-[2-[[[1-(2-amino-4-thiazolyl)-2-[(2-methyl-4-oxo-1-sulfo-3-azetidinyl)amino]-2-oxoethylidene]amino]-oxy-2-methyl-1-oxopropyl]hydrazide, disodium salt;

1,4-dihydro-6,7-dihydroxy-4-oxo-2,3-quinolinedicarboxylic acid, 2-[[2R-[2α,3α(Z)]]-2-[[[1-(2-amino-4-thiazolyl)-2-[(2-methyl-4-oxo-1-sulfo-3-azetidinyl)amino]-2-oxoethylidene]amino]-oxy]-2-methyl-1-oxopropyl]hydrazide], disodium salt;

(2S-trans)-1,4-Dihydro-6,7-dihydroxy-4-oxo-3-cinnolinecarboxylic acid, 2-[[2-[[[-1-(2-amino-4-thiazolyl)-2-[(2-methyl-4-oxo-1-sulfo-3-azetidinyl)amino]-2-oxoethylidene]amino]oxy]-2-methyl-1-oxopropyl]hydrazide, monopotassium salt;

(2S-trans)-5,6-dihydroxy-2-benzofurancarboxylic acid, 2-[2-[[[1-(2-amino-4-thiazolyl)-2-[(2-methyl-4-oxo-1-sulfo-3-azetidinyl)amino]-2-oxoethylidene]amino]oxy]-2-methyl-1-oxopropyl]hydrazide, monopotassium salt;

[2R-(2α,3α(Z)]-2-[2-[2-[2-[[[1-(2-amino-4-thiazolyl)-2--[(2-methyl-4-oxo-1-sulfo-3-azetidinyl)amino]-2-oxoethylidene]amino]oxy]-2-methyl-1-oxopropyl]hydrazino]-2-oxoethyl]-2,3-dihydro-5,6-dihydroxy-2-methyl-1H-isoindolium, inner salt; and

[2R-[2α,3α(Z)]]-2-[[[1-(2-amino-4-thiazolyl)-2-[(2-methyl-4-oxo-1-sulfo-3-azetidinyl)amino]-2-oxoethylidene]amino]oxy]-2-methylpropanoic acid, 2-[(1,3-dihydro-5,6-dihydroxy-2H-isoindol-2-yl)acetyl]hydrazide.

13. A method of treating bacterial infections, which comprises administering to a mammalian host an effective amount of a compound according to claim 1.

* * * * *